US010456284B2

(12) United States Patent
Farag Eells et al.

(10) Patent No.: US 10,456,284 B2
(45) Date of Patent: Oct. 29, 2019

(54) DEPLOYMENT HANDLE FOR A PROSTHESIS DELIVERY DEVICE

(71) Applicant: Cook Medical Technologies LLC, Bloomington, IN (US)

(72) Inventors: Jacqueline Farag Eells, Bloomington, IN (US); Per Hendriksen, Herlufmagle (DK); Erik E. Rasmussen, Slagelse (DK); Marianne Soerensen, Ringsted (DK)

(73) Assignee: Cook Medical Technologies LLC, Bloomington, IN (US)

(*) Notice: Subject to any disclaimer, the term of this patent is extended or adjusted under 35 U.S.C. 154(b) by 223 days.

(21) Appl. No.: 15/654,134

(22) Filed: Jul. 19, 2017

(65) Prior Publication Data
US 2017/0312108 A1 Nov. 2, 2017

Related U.S. Application Data

(63) Continuation of application No. 14/623,091, filed on Feb. 16, 2015, now Pat. No. 9,717,614.

(60) Provisional application No. 61/940,738, filed on Feb. 17, 2014, provisional application No. 61/940,480, filed on Feb. 16, 2014.

(51) Int. Cl.
A61F 2/95 (2013.01)
A61F 2/954 (2013.01)

(52) U.S. Cl.
CPC ............... A61F 2/95 (2013.01); A61F 2/954 (2013.01); A61F 2002/9511 (2013.01); A61F 2002/9517 (2013.01)

(58) Field of Classification Search
CPC .... A61F 2/954; A61F 2/95; A61F 2002/9517; A61F 2002/9511
See application file for complete search history.

(56) References Cited

U.S. PATENT DOCUMENTS

| | | | |
|---|---|---|---|
| 5,776,142 A | 7/1998 | Gunderson | |
| 6,146,415 A | 11/2000 | Fitz | |
| 6,395,017 B1 | 5/2002 | Dwyer et al. | |
| 6,402,760 B1 | 6/2002 | Fedida | |
| 6,599,296 B1 | 7/2003 | Gillick et al. | |

(Continued)

FOREIGN PATENT DOCUMENTS

| | | |
|---|---|---|
| DE | 4420142 A1 | 12/1995 |
| EP | 1302178 A2 | 4/2003 |

(Continued)

OTHER PUBLICATIONS

Communication for EP Application No. 15275038.6, dated Mar. 26, 2018, 3 pages.

(Continued)

Primary Examiner — Phong Son H Dang
(74) Attorney, Agent, or Firm — Brinks Gilson & Lione

(57) ABSTRACT

A handle assembly for a delivery device the sequential release of trigger wires from a prosthesis to release the prosthesis from the delivery device. The handle assembly has two handles, one of which is a rotating handle. The rotating handle has a first and second trigger wire release mechanisms which operate to sequentially release a first and second trigger wire, respectively, and a locking mechanism. The other handle has a locking mechanism that prevents that operation of the second trigger wire release mechanism until the first trigger wire has been released.

16 Claims, 17 Drawing Sheets

(56) References Cited

U.S. PATENT DOCUMENTS

| | | |
|---|---|---|
| 6,669,716 B1 | 12/2003 | Gilson et al. |
| 6,866,669 B2 | 3/2005 | Buzzard et al. |
| 6,872,224 B1 | 3/2005 | Moretra et al. |
| 7,172,580 B2 | 2/2007 | Hruska et al. |
| 8,419,783 B2 | 4/2013 | Frye et al. |
| 2003/0233140 A1 | 12/2003 | Hartley et al. |
| 2004/0073289 A1 | 4/2004 | Hartley |
| 2004/0098079 A1 | 5/2004 | Hartley et al. |
| 2005/0060016 A1 | 3/2005 | Wu et al. |
| 2006/0286145 A1 | 12/2006 | Horan et al. |
| 2007/0073389 A1 | 3/2007 | Bolduc et al. |
| 2007/0156224 A1 | 7/2007 | Cioanta et al. |
| 2007/0156225 A1 | 7/2007 | George et al. |
| 2007/0255390 A1 | 11/2007 | Ducke et al. |
| 2011/0288558 A1 | 11/2011 | Nimgaard |

FOREIGN PATENT DOCUMENTS

| | | | |
|---|---|---|---|
| EP | 1358903 A2 | 11/2003 | |
| EP | 1806114 A2 | 7/2007 | |
| EP | 2623071 A2 | 8/2013 | |
| GB | 2474252 A | 4/2011 | |
| WO | WO 98/20811 | 5/1998 | |
| WO | WO 99/49808 | 10/1999 | |
| WO | WO 00/61035 | 10/2000 | |
| WO | WO 00/67675 | 11/2000 | |
| WO | WO 2004/028399 A2 | 4/2004 | |
| WO | WO 2005/032425 A1 | 4/2005 | |
| WO | WO 2005/037142 A2 | 4/2005 | |
| WO | WO 2007/047023 A2 | 4/2007 | |
| WO | WO 2007/070788 A2 | 6/2007 | |
| WO | WO 2008/017683 A1 | 2/2008 | |
| WO | WO 2009/001309 A1 | 12/2008 | |
| WO | WO 2012/036741 A2 | 3/2012 | |

OTHER PUBLICATIONS

Extended European Search Report from corresponding EP 15275038.6 dated Jul. 6, 2015, 7 pages.
Communication from corresponding EP 15275038.6 dated Aug. 7, 2017, 3 pages.
Combined Search and Examination Report for GB 0917557.1 dated Feb. 5, 2010 (8 pages).
Further Search Report for GB 0917557.1 dated Sep. 15, 2010 (2 pages).
Preliminary Amendment for U.S. Appl. No. 12/899,203 dated Aug. 15, 2011 (7 pages).
Restriction Requirement for U.S. Appl. No. 12/899,203 dated Jul. 12, 2012 (6 pages (6 pages).
Response to Restriction Requirement for U.S. Appl. No. 12/899,203 dated Aug. 10, 2012 (2 pages).
Office Action for U.S. Appl. No. 12/899,203 dated Sep. 12, 2012 (16 pages).
Response to Office Action for U.S. Appl. No. 12/899,203 dated Dec. 12, 2012 (11 pages).
Office Action for U.S. Appl. No. 12/899,203 dated Jan. 14, 2013 (10 pages).
Response to Office Action for U.S. Appl. No. 12/899,203 dated Mar. 14, 2013 (8 pages).
Advisory Action for U.S. Appl. No. 12/899,203 dated Mar. 28, 2013 (3 pages).
Pre-Brief Conference Request for U.S. Appl. No. 12/899,203 dated Apr. 15, 2013 (5 pages).
Decision for U.S. Appl. No. 12/899,203 dated May 24, 2013 (2 pages).
Office Action for U.S. Appl. No. 12/899,203 dated Sep. 3, 2013 (10 pages).
Response to Office Action for U.S. Appl. No. 12/899,203 dated Dec. 24, 2013 (9 pages).
Office Action for U.S. Appl. No. 12/899,203 dated May 7, 2014 (11 pages).
Response to Office Action for U.S. Appl. No. 12/899,203 dated Oct. 3, 2014 (11 pages).
Notice of Allowance for U.S. Appl. No. 12/899,203 dated Oct. 22, 2014 (7 pages).

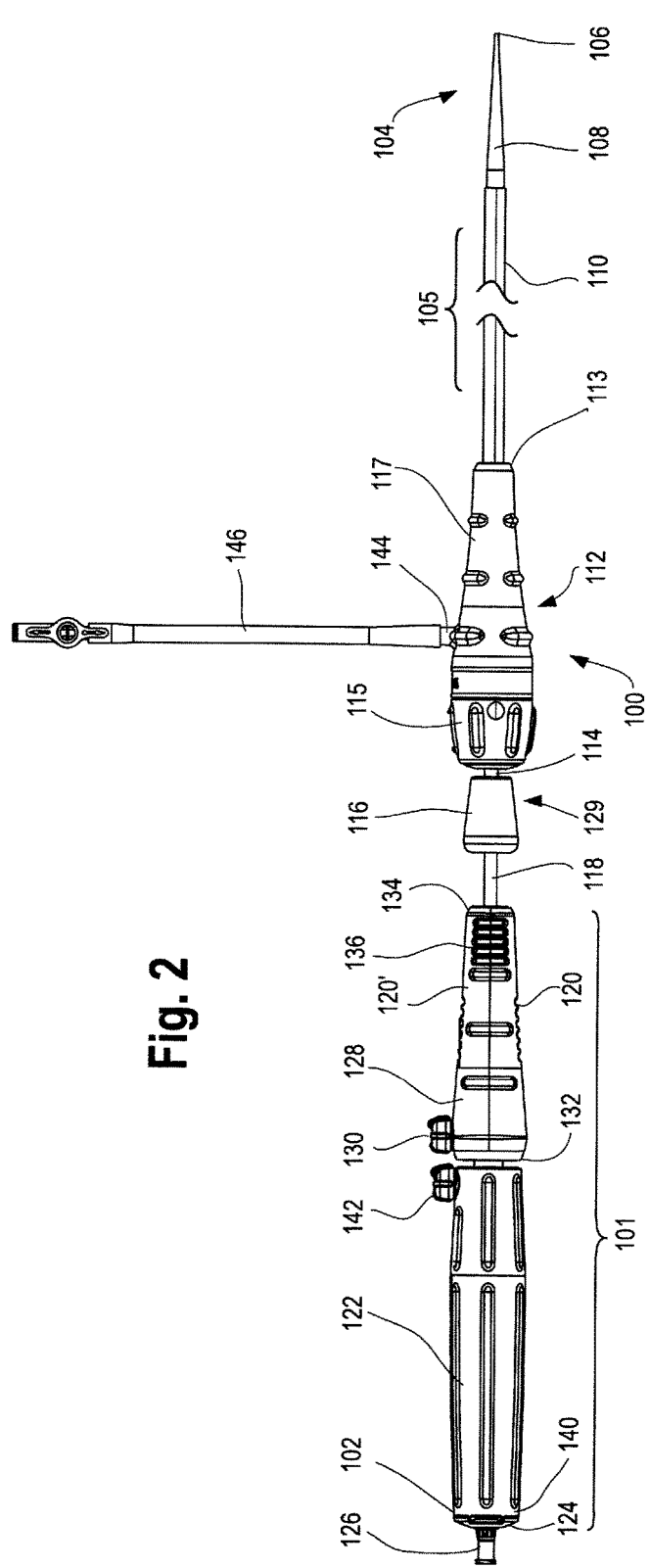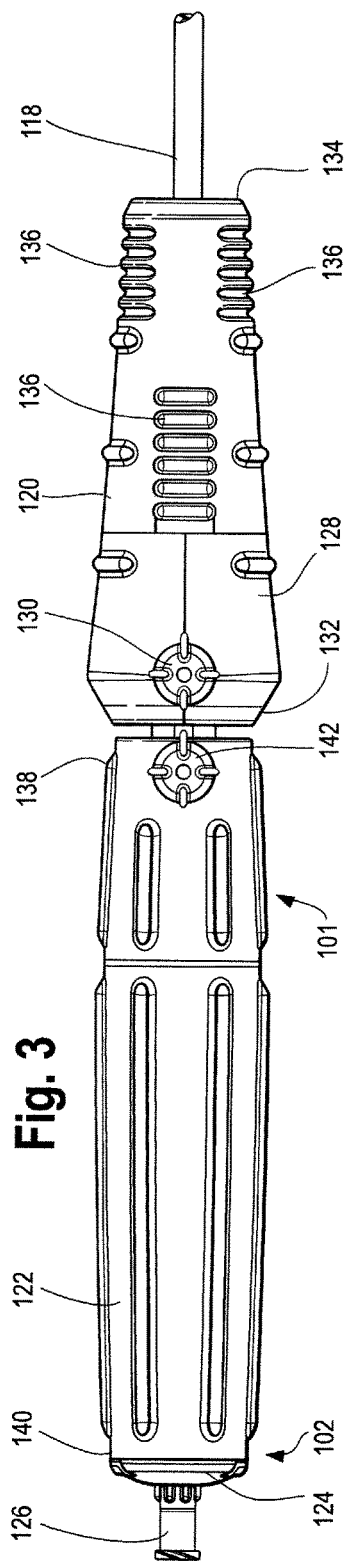

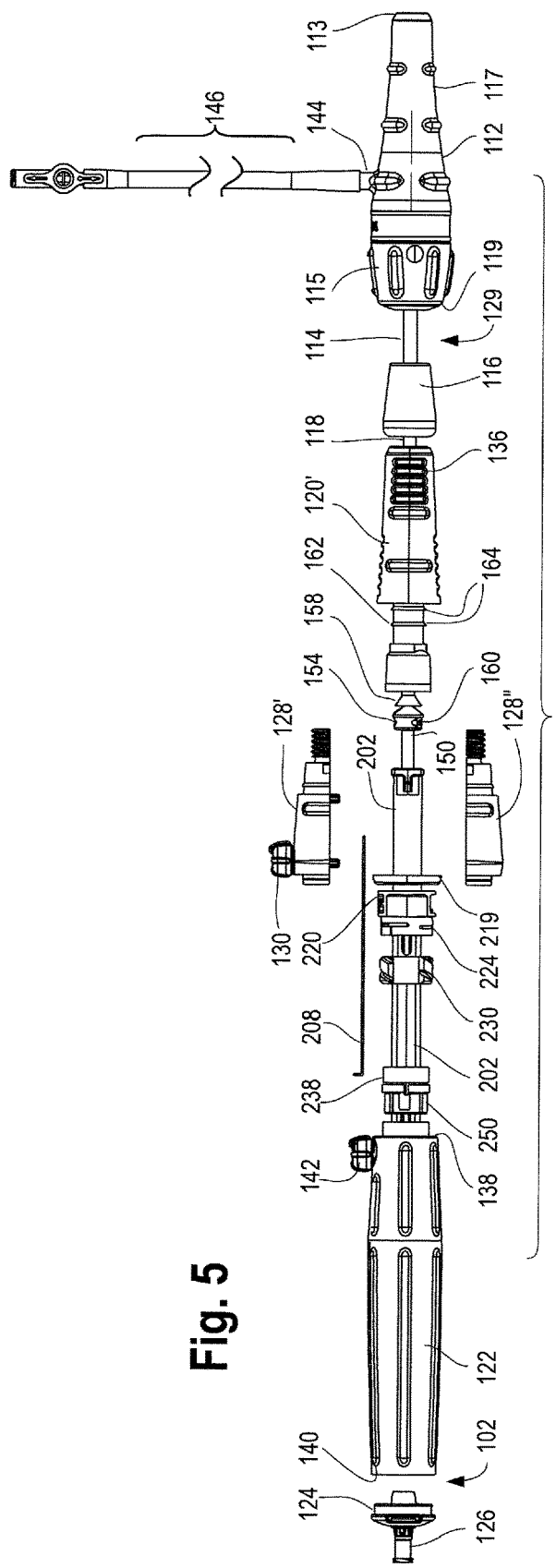

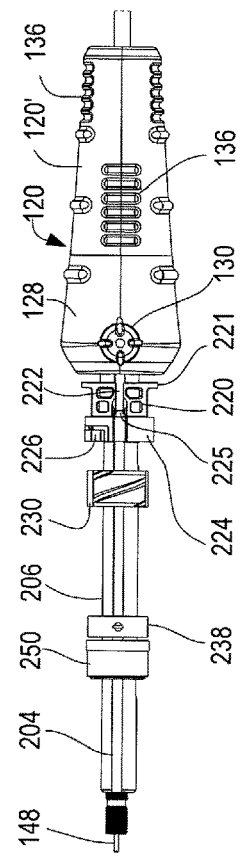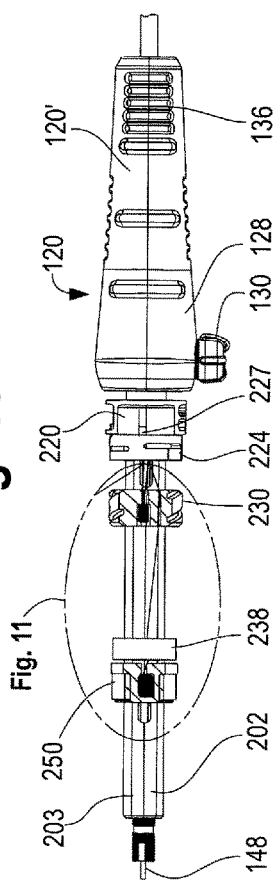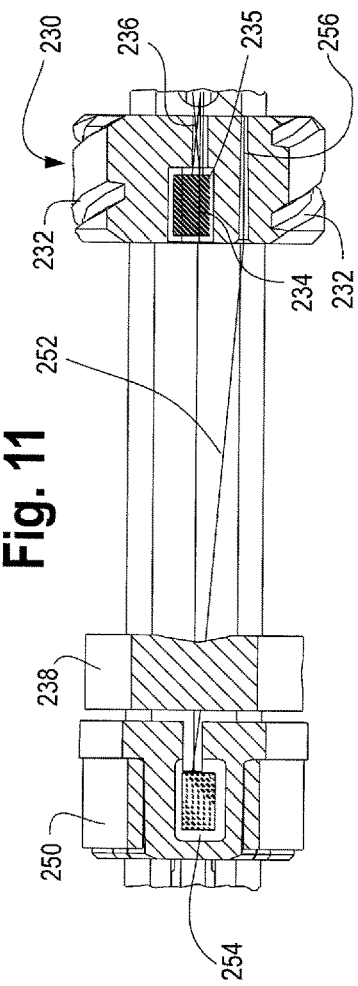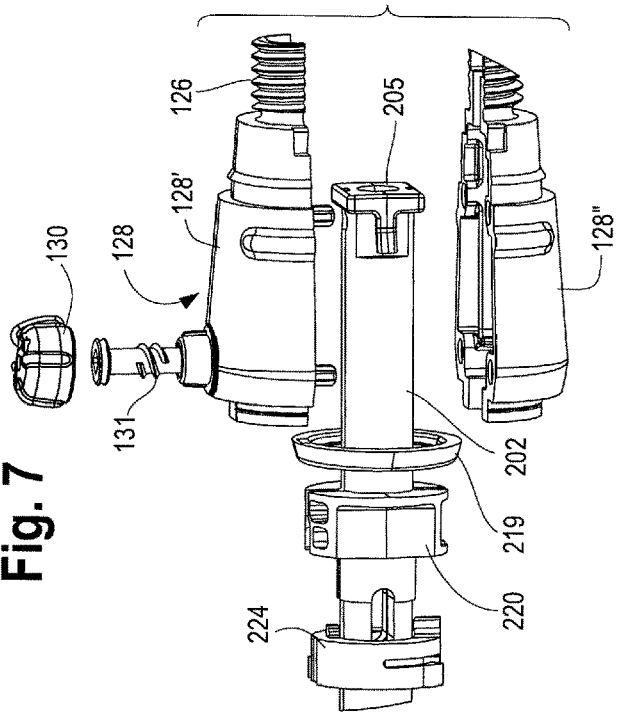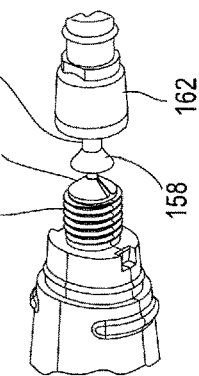

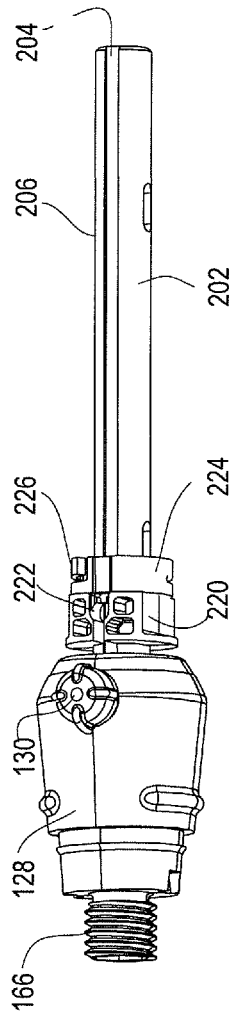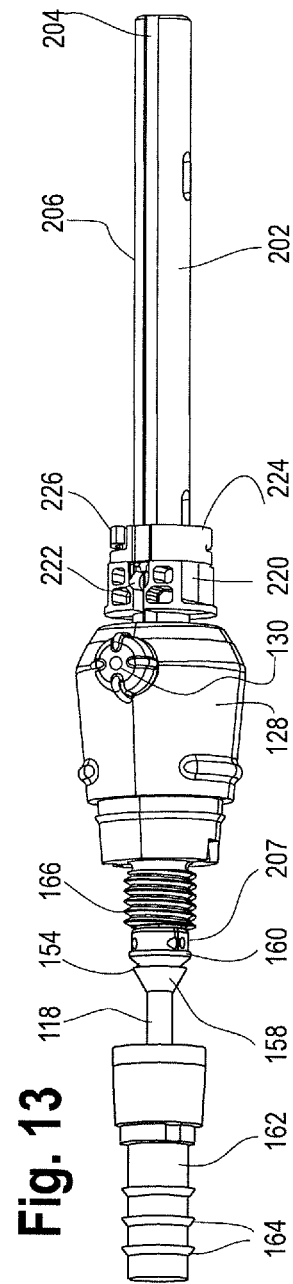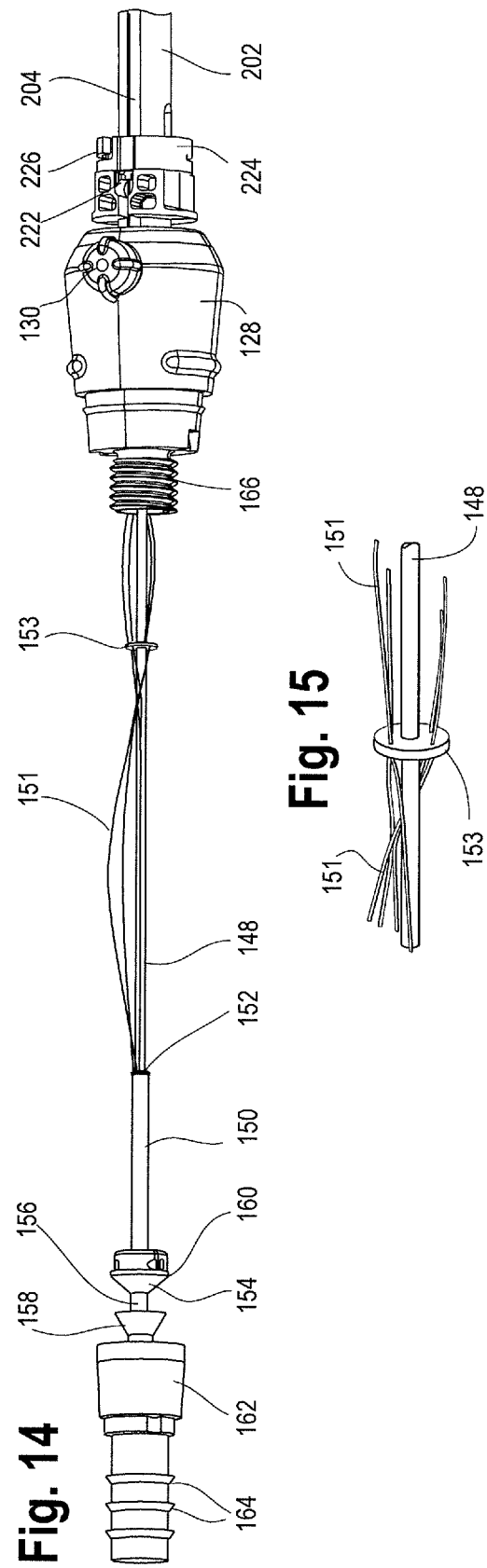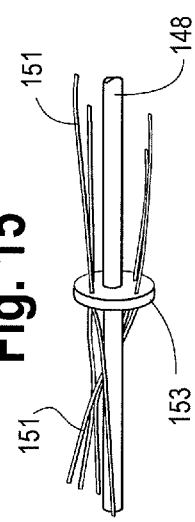

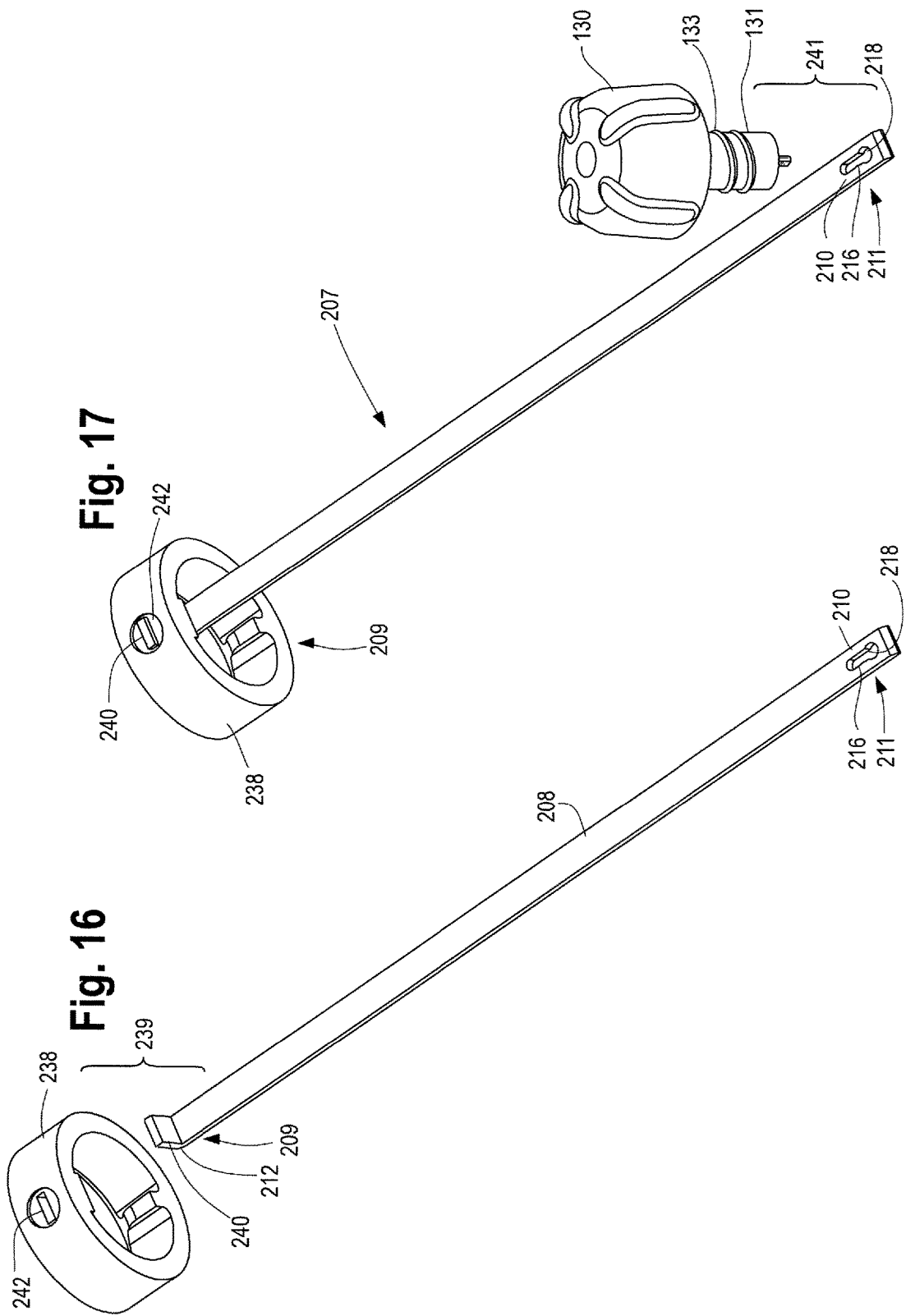

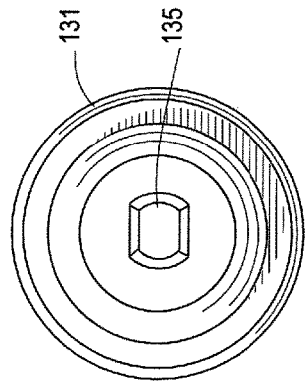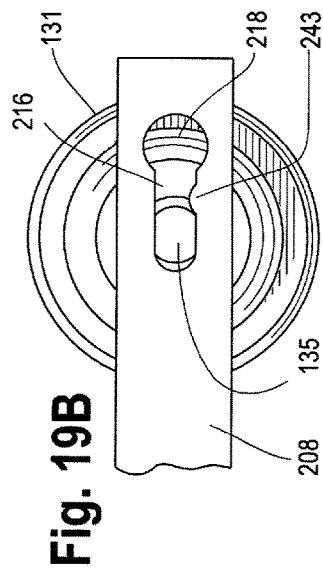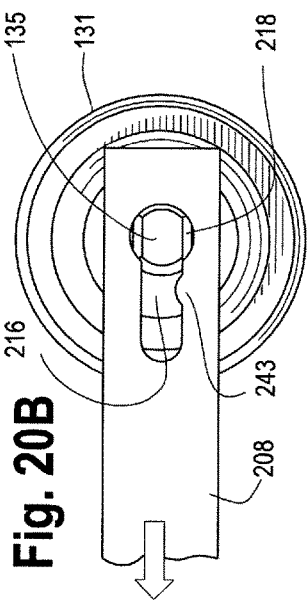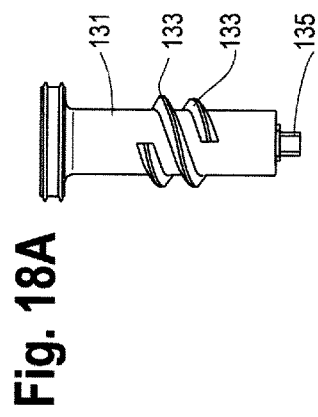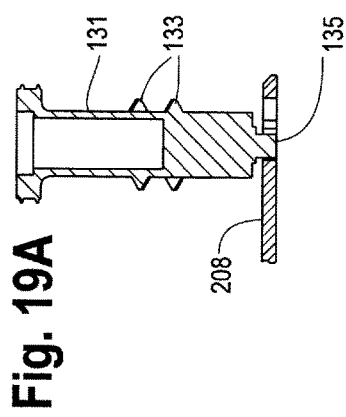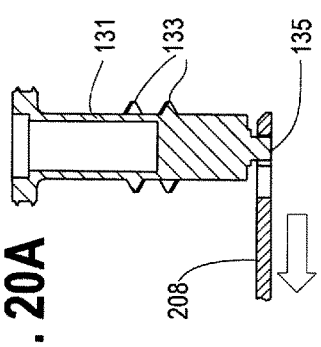

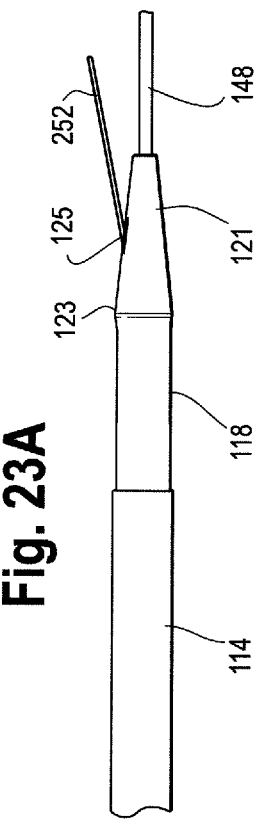
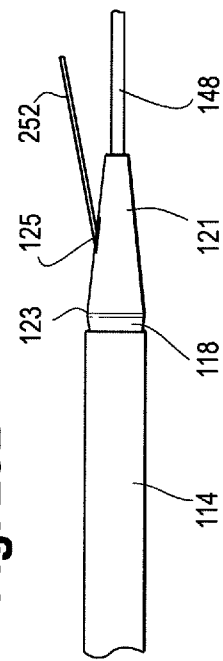
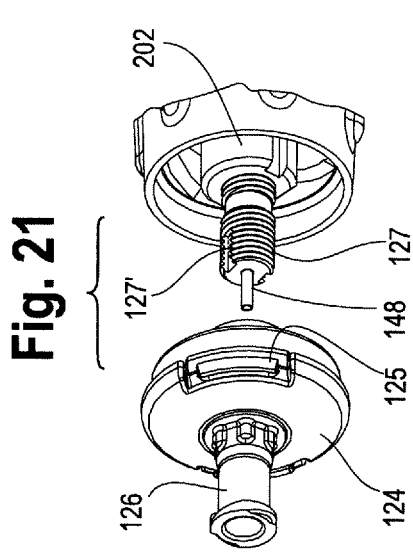
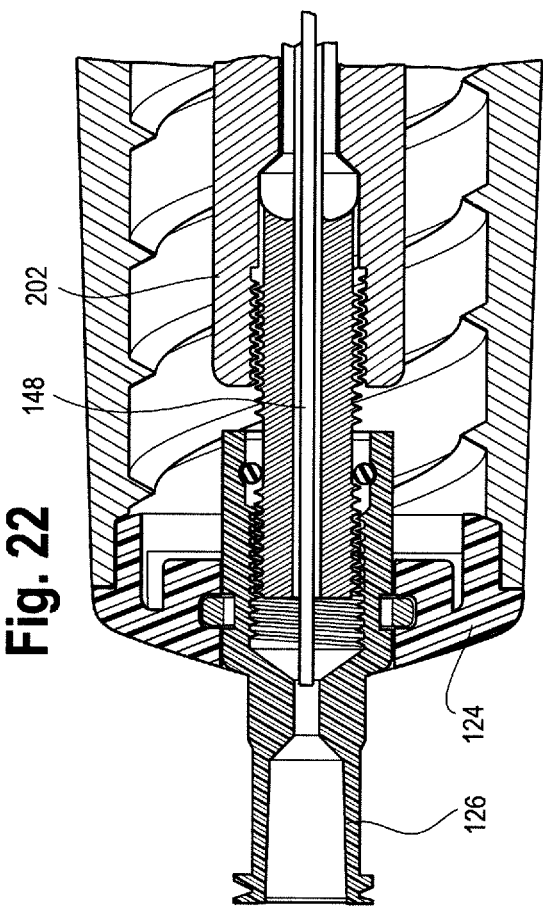

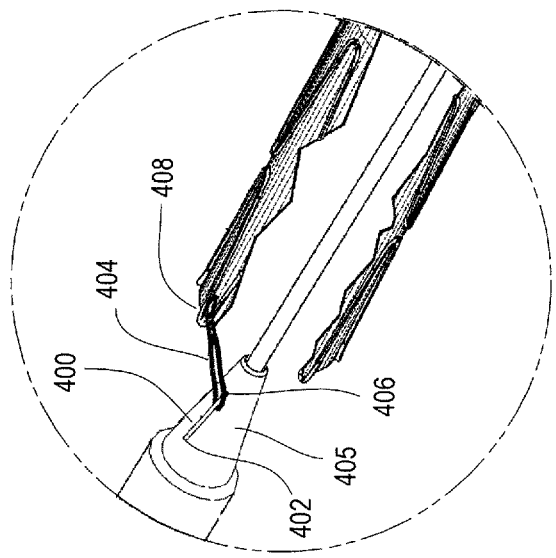
Fig. 25
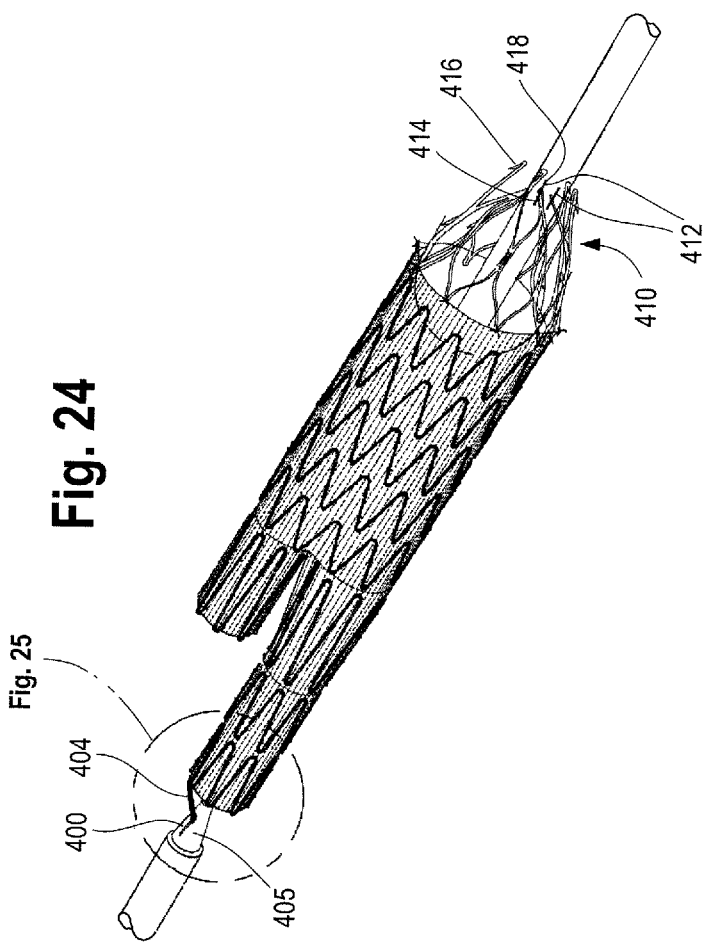
Fig. 24
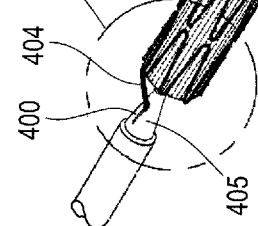

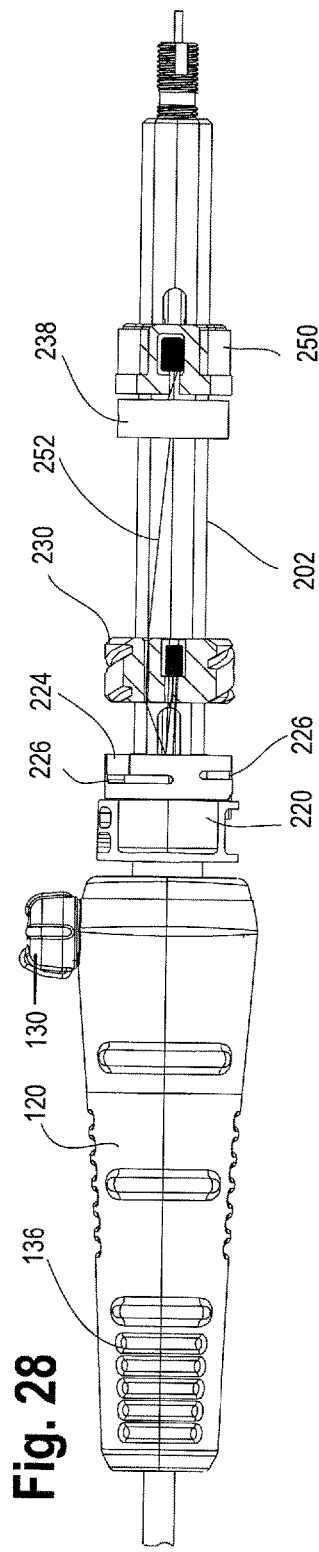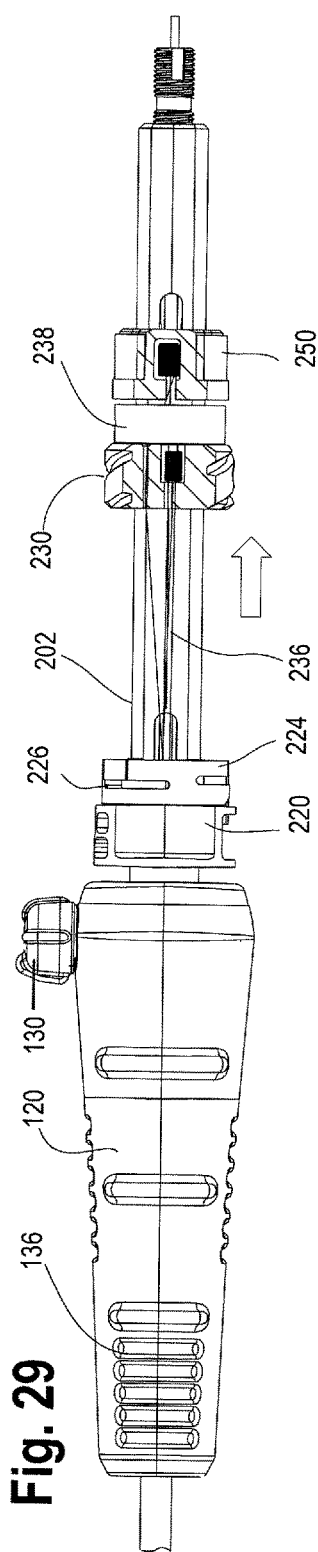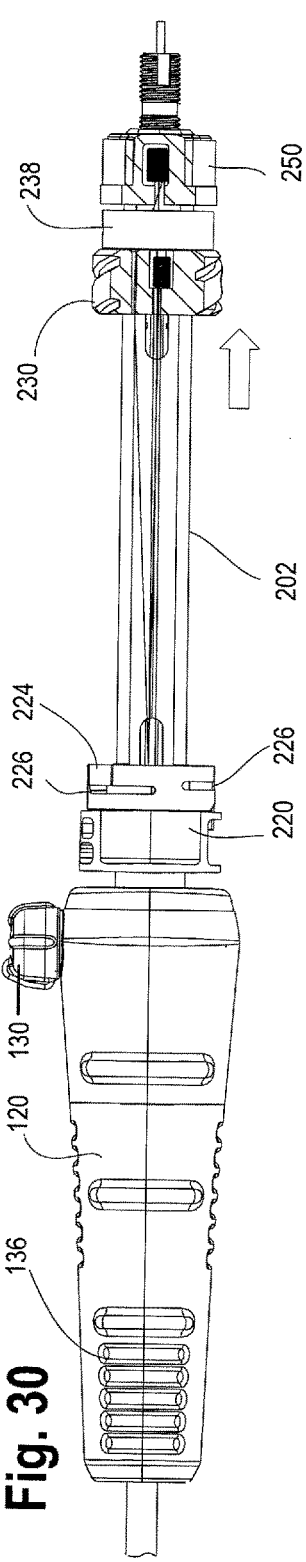

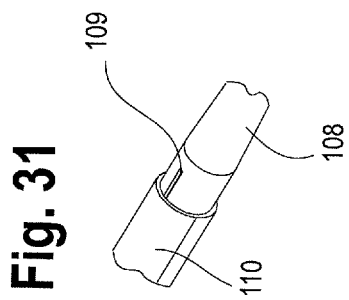

DEPLOYMENT HANDLE FOR A PROSTHESIS DELIVERY DEVICE

RELATED APPLICATIONS

This application is a continuation application of U.S. Ser. No. 14/623,091 filed Feb. 16, 2015, which claims the benefit of priority of U.S. Provisional Application Ser. No. 61/940,480 filed Feb. 16, 2014, and U.S. Provisional Application Ser. No. 61/940,738 filed Feb. 17, 2014, which are incorporated by reference in their entirety.

BACKGROUND

Technical Field

The present invention relates to a deployment handle for a delivery device for a prosthesis such as a stent graft, and to a delivery device including such a handle.

Background

The use of delivery devices or introducers employing catheters has long been known for a variety of medical procedures, including procedures for establishing, re-establishing or maintaining passages, cavities or lumens in vessels, organs or ducts in human and veterinary patients, occlusion of such vessels, delivering medical treatments, and other interventions. For these procedures, it has also long been known to deliver an implantable medical device by means of a catheter, often intraluminally. For example, a stent, stent-graft, vena cava filter or occlusion device may be delivered intraluminally from the femoral artery for deployment.

For procedures in which a prosthesis or other medical device is implanted into a patient, the device to be implanted is normally held on a carrier catheter or cannula of the introducer in a compressed state and then released from the carrier catheter so as to expand to its normal operating state, prior to withdrawal of the catheter from the patient to leave the implant in position. In many devices, the steps to carry out the implantation my occur, for example, first by retracting a retractable sheath to expand or partially expand the device, and then performing further steps to, for example, release one or both ends of the device, deploy an anchoring stent, or the like. In most cases, it is desirable that such steps follow a specific order as instructed by the manufacturer of the device, but the user of the device is often not restricted from performing steps out of order, and often may do so.

BRIEF SUMMARY

The present invention relates to a deployment handle assembly for a delivery device for a prosthesis such as a stent graft, and to a delivery device including such a handle assembly. The handle assembly includes first and second handles. The second handle is rotatable and facilitates sequential release of trigger wires from the proximal and distal ends of a prosthesis from the delivery device. Advantages of the novel handle assembly include simplification of deployment, decreased trigger wire release force, decreased sheath pullback force, ensuring the complete performance of one step prior to the performance of the next, effective "bailout" if the system fails allowing the process to still be successfully completed, among others.

In one example, a handle assembly for a prosthesis delivery device comprising a distal end and a proximal end includes a first handle comprising a first locking mechanism and a rotatable handle. The rotatable handle has a second locking mechanism preventing movement of the rotatable handle, a first trigger wire release mechanism attached to at least one trigger wire, wherein the at least one first trigger wire extends from the first trigger wire release mechanism, and a second trigger wire release mechanism attached to at least one trigger wire, wherein the at least one second trigger wire extends from the second trigger wire release mechanism. The unlocking of the second locking mechanism permits a first rotation of the rotatable handle and the release the at least one first trigger wire, and the unlocking of the first locking mechanism permits a second rotation of the rotatable handle and the release of the at least one second trigger wire. The first locking mechanism cannot be unlocked until the second locking mechanism is unlocked and the at least one first trigger wire is released.

BRIEF DESCRIPTION OF THE DRAWINGS

FIG. 2 shows a side view of an exemplary delivery device.

FIG. 3 is a top view of the handle assembly of the delivery device of FIG. 2.

FIG. 5 is a partial exploded side view of the handle assembly of the delivery device of FIG. 2.

FIG. 6 is a partial side view of the inner structure of the first handle of the handle assembly.

FIG. 7 is a partial exploded side view of the first handle of the handle assembly.

FIG. 8 is a partial perspective view of the inner structure of a first handle of the handle assembly.

FIG. 9 is a partial top view of the handle assembly and the interior structure of the second handle of the handle assembly.

FIG. 10 is a partial side view of the handle assembly and the interior structure of the second handle of the handle assembly.

FIG. 11 is an enlarged view of a portion of FIG. 10.

FIG. 12 shows a partial perspective view of the interior of the second handle.

FIG. 13 shows a partial perspective view of the handle assembly.

FIG. 14 shows a partial perspective view of the handle assembly.

FIG. 15 is a partial view of the inner cannula and trigger wire assembly of the handle assembly.

FIG. 16 is a perspective view of the safety rod.

FIG. 17 is another perspective view of the safety rod and the first safety knob.

FIG. 18A is a side view of the threaded pin of the first safety knob.

FIG. 18B is a bottom view of the threaded pin of the first safety knob.

FIG. 19A is a side view of the threaded pin of the first safety knob engaging the safety rod in a first position.

FIG. 19B is a bottom view of the threaded pin of the first safety knob engaging the safety rod in a first position.

FIG. 20A is a side view of the threaded pin of the first safety knob engaging the safety rod in a second position.

FIG. 20B is a bottom view of the threaded pin of the first safety knob engaging the safety rod in a second position.

FIG. 21 is a perspective view of the proximal end and end cap of the delivery device.

FIG. 22 is a side view of the interior of a proximal portion of the second handle of the handle assembly.

FIGS. 23A and 23B are side views of a tapered distal end portion of a positioner of the delivery device.

FIG. 24 is a perspective view of a stent-graft disposed at the stent-graft retention region of a delivery device.

FIG. 25 is an enlarged perspective view of the attachment region for the distal end of the stent graft of FIG. 24.

FIG. 28 shows the operation of a deployment step of the second handle of the handle assembly.

FIG. 29 shows another operation of a deployment step of the second handle.

FIG. 30 shows another operation of a deployment step of the second handle.

FIG. 31 is an enlarged view of a portion of the nose cone dilator shown in FIG. 4.

DETAILED DESCRIPTION

In this description, when referring to an introducer or delivery device, the term "distal" is used to refer to an end of a component which in use is furthest from the surgeon during the medical procedure, including within a patient. The term "proximal" is used to refer to an end of a component closest to the surgeon and in practice in or adjacent an external manipulation part of the deployment or treatment apparatus.

On the other hand, when referring to an implantable medical device such as a stent or stent-graft, the term "proximal" refers to a location that in use is closest to the patient's heart, in the case of a vascular implant, and the term "distal" refers to a location furthest from the patient's heart.

For the purposes of this disclosure, the disclosure of co-pending application Ser. No. 12/899,203 entitled "Deployment Handle for Introducer" is incorporated by reference in its entirety, and in particular FIGS. 9-19 and 24-34 and their accompanying text, the disclosure of which is incorporated by reference in its entirety.

Figure 1:
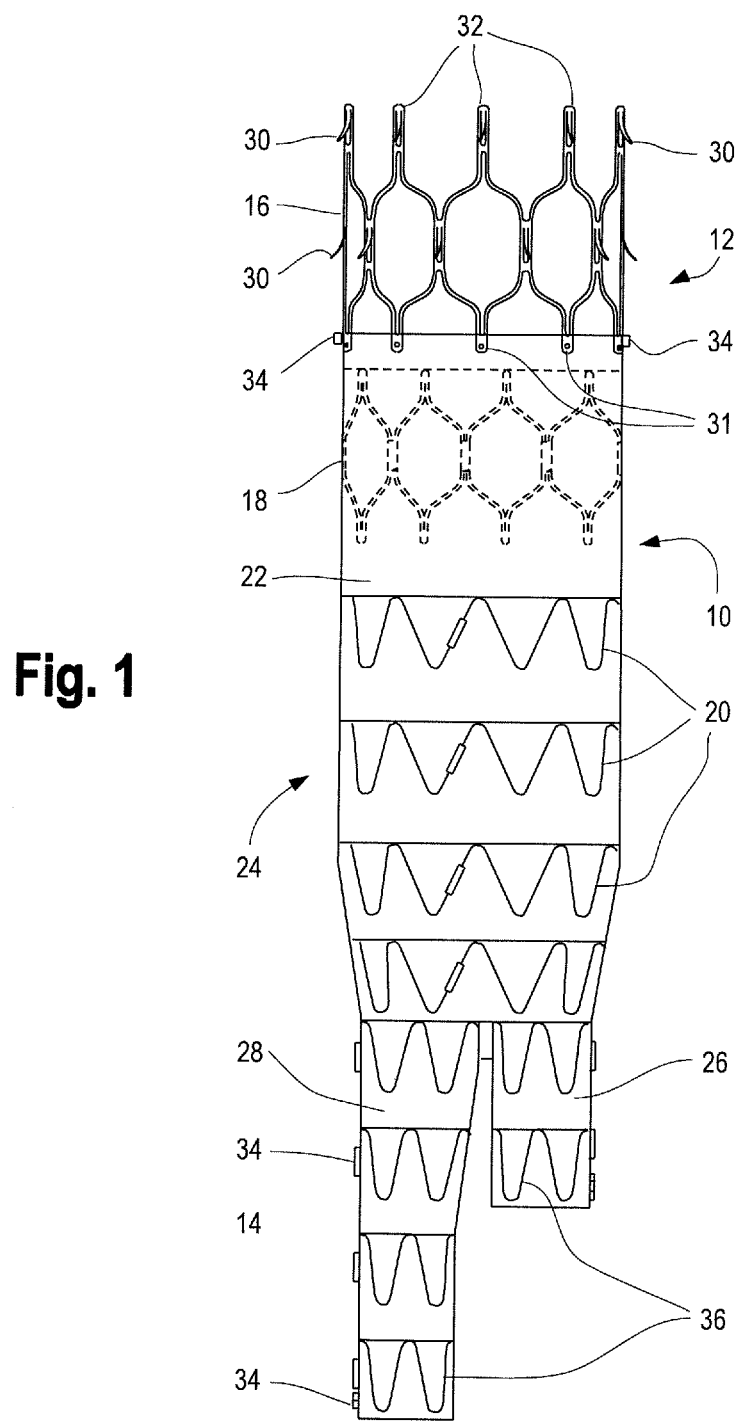
FIG. 1 shows an exemplary stent graft for use with the delivery device of the present invention.

FIG. 1 shows an exemplary stent-graft for which the delivery system of the present invention may be used. Stent-graft 10 has a proximal end 12 (that end with the bare anchoring stent 16 extending therefrom), a distal end 14, and a series of stents extending the length of the stent-graft 10 and attached to the graft 22. Extending from the proximal end 12 of the stent-graft 10 is an exposed anchoring stent 16. Anchoring stent 16 is attached to the graft material by, for example, suturing the distal apices 31 of the anchoring stent 16 to the graft material. Next adjacent the anchoring stent 16 is sealing stent 18. Sealing stent 18 may be internal or external to the graft 22. A series of body stents 20 also are attached to the graft material and may be sutured to the graft material or held to the graft material in other known ways. The series of body stents 20 may be internal or external to the graft 22, or both. As shown in FIG. 1, sealing stent 18 is internal and body stents 20 are external to the graft 22. As shown in FIG. 1, stent-graft 10 is bifurcated having two limbs 26, 28 extending from the tubular main body 24. One of the limbs 26 may be shorter than the other limb 28, or both may be the same length. Anchoring stent 16 may have one or more barbs 30 for attaching the stent-graft 10 to a body vessel. Barbs 30 may be at or near the proximal apices 32 of the anchoring stent 16 and/or be located at some midpoint along the anchoring stent 16. Radiopaque markers 34 may be placed on various parts of the device, including the proximal end, along one or both limbs, at the bifurcation, or other places. Limbs 26 and 28 may also have a series of stents 36 along their length, either or both internal and external. Although FIG. 1 shows a bifurcated stent-graft, the stent-graft also may be a single tube.

The stent-graft is placed on a delivery device, usually by the manufacturer prior to sale. The stent-graft is disposed on the device at a stent-graft retention region generally at the distal end of the delivery device. One or both ends of the stent graft may be secured to the system by things such as sutures, trigger wires, retention caps or other capture mechanisms, and then the device is covered by a sheath or sleeve that is removed prior to implantation. As described here, the proximal end of the stent-graft (that end closest to the patient's heart in deployment) is retained onto the delivery device with one or more proximal trigger wires as will be explained below. The one or more proximal trigger wires run from the proximal end of the stent-graft to the handle assembly and are engaged by a proximal trigger wire(s) release mechanism. The distal end of the stent-graft also is retained onto the delivery device with one or more trigger wires which run from the distal end of the stent-graft to the handle assembly and are engaged by a distal trigger wire(s) release mechanism.

In general and described in more detail below with reference to the reference numbers and figures, the delivery device 100 includes a proximal end and a distal end. The handle assembly 101 described here is located adjacent the proximal end of the device. An inner cannula 148 (not shown in FIG. 2, but shown in FIGS. 4, 6, 22, 26 and 27) having a lumen (not shown) extends from the proximal end 102 to the distal end 104 of the device 100. The inner cannula 148 is attached to a tapered nose cone dilator 108 at the distal end of the device. The lumen of the inner cannula 148 may accommodate one or more guide wires and/or fluids for flushing or otherwise. The handle assembly 101, as described in detail below includes first 120 and second handles 122. The second handle 122 is at the proximal end of the device and the first handle 120 is distally adjacent the second handle 122. The first handle 120 is fixed relative to the delivery system and the second handle housing is rotatable relative to the delivery system and provided with inner threads. A positioner 118 is disposed over the inner cannula 148, which positioner 118 extends from the first handle 120 to just proximal of the stent-graft retention region 105. For a length of the positioner 118, a stiffening rod 156 (not shown in FIG. 2, but shown in FIGS. 6, and 11) is disposed over the inner cannula 148 and within the positioner 118 for stability and maneuverability.

Located approximately one third to midway along the delivery device from the proximal end, a housing 112 is slideably disposed over the positioner 118. Housing 112 provides a grip 117 for a user of the delivery system and may include a valve system. A slidable and retractable sheath 110 extends from the distal end of the housing 112 to the nose cone dilator 108 and engages a proximal portion of the nose cone dilator 108. The delivery device may include a deployment assist device 129, which will be described more fully here, proximal to the housing. The deployment assist device 129 includes an assist device housing 129 which has a valve such as a disk valve, and a sleeve 114. The deployment assist device 129 is disposed over the positioner 118 and is slidable along the positioner 118. In one position the sleeve may extend into the housing through an aperture at the proximal end of the housing and through the housing valve system. The deployment assist device 129 reduces friction between the valve and the positioner 118 and makes retraction of the sheath 110 smoother and easier. The deployment assist device 129 also makes removal of the delivery device sub-assembly upon completion of the implantation procedure. Other features of the delivery system and in particular the inventive handle assembly are described more fully below with reference to FIGS. 2-33.

Figure 4:
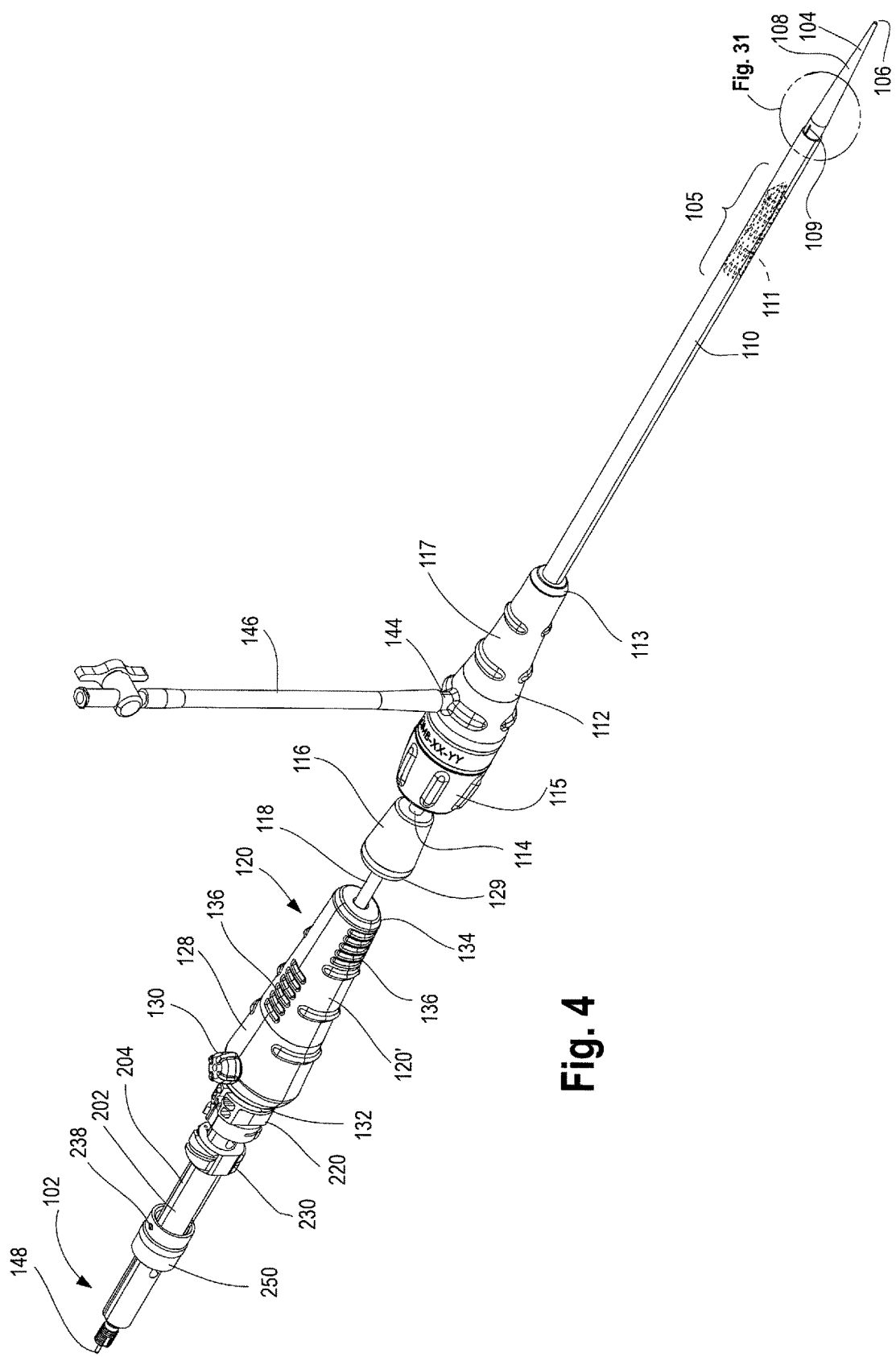
FIG. 4 is a partial perspective view of the delivery device of FIG. 2.

FIG. 2 is a side view of an exemplary delivery device 100 for a prosthesis with an exemplary handle assembly 101. Delivery device 100 has a proximal end 102 and a distal end 104. As shown, the delivery device 100 includes stent graft retention region 105, distal tip 106, tapered nose cone dilator 108, sheath 110, and housing 112, housing gripping portion 117, positioner 118, first or forward handle 120, second or rearward handle 122, back end cap 124, and pin vise 127 (shown in FIG. 21). An inner cannula (not shown) extends from the proximal end 102 to the distal end 104 and engages the nose cone dilator 108. Inner cannula has an inner lumen (not shown) which may accommodate a guide wire in use and may be used for flushing or injection of fluids. Inner cannula may be made of any flexible material, for example nitinol, and may be either straight or have a curve imparted to a portion of it. As shown, nose cone dilator 108 is tapered to facilitate entry into and travel through a body vessel. Nose cone dilator 108 may include radiopaque material or be equipped with a radiopaque marker (not shown) to facilitate visualization of the nose cone dilator 108 in use. Nose cone dilator 108 and distal tip 106 are preferably atraumatic. As shown in FIGS. 4 and 31, nose cone dilator 108 may include a longitudinal groove 109 in the surface of the dilator 108 to accommodate fluid such as for flushing purposes.

Sheath 110 is attached to housing 112. Sheath 110 extends for a length from the distal end 113 of the housing 112 to generally just proximal of the nose cone dilator 108. Housing 112 may include a gripping portion 117 for a physician to grip while retracting the sheath 110 during deployment. Housing 112 may include a hemostatic valve (not shown) within the housing 112 in a proximal portion 115 of the housing 112. A suitable hemostatic valve is shown and disclosed in Hruska et al., U.S. Pat. No. 7,172,580, in particular in FIG. 3 of that disclosure and the accompanying text, which disclosure is incorporated by reference herein in its entirety.

FIG. 2 shows a side view of the exterior of the handle assembly 101. FIG. 3 is a top view of the exterior of the handle assembly 101. As shown, the handle assembly 101 includes first handle 120 and second handle 122. First handle 120 is fixed relative to the delivery system. Second handle 122 is rotatably moveable. First handle 120 has a proximal end 132, a distal end 134, a forward portion 120', first handle housing 128, grips 136, and first safety knob 130. Second handle 122 is disposed proximally of first handle 120 and is rotatably movable relative to first handle 120. Second handle 122 has a distal end 138, a proximal end 140, second safety knob 142, end cap 124 and a cannula hub 126 which is attached to pin vise 127, preferably by adhesive or glue.

FIG. 21 shows the proximal end 102 of the delivery system including the cannula hub 126, back end cap 124, and pin vise 127. Back end cap 124 may be snap fit into engagement with the proximal end 140 of second handle 122. End cap 124 may have indentations 125 that facilitate removal of end cap 124 should the need arise, such as in the event of an emergency "bailout" procedure as will be described in further detail below with reference to FIGS. 34A-F. Pin vise 127 is attached to the end of the delivery device by a threaded fit 127' and with adhesive. Inner cannula 148 extends through the back end cap 124 to the pin vise 127. The proximal end of slider rod 202 also is shown in FIG. 21 and is threadedly secured as shown in FIG. 22, which is a side view of the internal structure of the proximal end 102 of the delivery device 100. Further securement and sealing to the threaded fits may be supplied by the addition of glue.

Referring back to FIG. 2, the delivery device 100 includes a deployment assist device 129 including assist sleeve 114 and deployment assist valve housing 116. Deployment assist valve sleeve 114 extends distally from deployment assist valve housing 116. The sleeve 114 is disposed over positioner 118 and slidably extends into housing 112 through a proximal aperture (not shown) in housing 112. The sleeve 114 is moveable between a first position in which the sleeve 114 is disposed outside of the housing 112 and a second position in which at least a portion of the sleeve 114 is disposed within the housing 112. When the sleeve 114 is disposed within the housing 112 it passes through the hemostatic valve assembly (not shown) within housing 112 and assists in the reduction of sheath pullback force. Without the sleeve 114, the valve assembly may exert an inward compressive sealing force against the outer surface of the positioner 118 due to the seal between the valve and the positioner 118. In general, as the quality of the seal improves, the friction between the positioner 118 and the valve increases. The higher the inward compressive force, and hence the seal of the valve on the positioner, the higher the frictional force, which creates greater frictional resistance to movement of the housing 112 to retract the sheath 110. The deployment assist sleeve 114 is disposed between the valve and the positioner 118. The compressive force of the valve is transferred to the sleeve 114, thereby reducing the frictional forces on the positioner 118 and making withdrawal of the sheath easier for the physician. A suitable deployment assist device as described here is disclosed in U.S. Pat. No. 8,419,783, which disclosure is incorporated by reference.

As further shown in FIG. 2, first handle 120 includes a forward portion 120', first handle housing 128, first safety knob 130, proximal end 132, distal end 134, and one or more grips 136. First handle (forward handle) 120 is forward or distal of second handle 122 and has one or more grips 136 for gripping by the user. First handle 120, as explained in more detail below is stationary. Second handle (rearward handle) 122 is back or proximal of the first handle 120, and has a distal end 138, a proximal end 140, a second safety knob 142, and a back end cap 124 disposed at the proximal end 136 of the second handle 122. Second handle 122, as further explained below, is rotatable relative to first handle 120.

Positioner 118 extends through the delivery device 100 from the first handle 120 to just proximal of the stent-graft retention region 105. Positioner 118 may include a length of greater stiffness than the rest of the positioner as discussed in more detail below. Housing 112 may include a port 144 and 146 flushing tube for the infusion of other fluids.

FIG. 4 is a perspective view of the delivery device 100. Delivery device is shown with the second handle 122 housing removed and without end cap 124. As shown, delivery device 100 has a proximal end 102, a distal end 104, distal tip 106, nose cone dilator 108, and sheath 110. As shown, a prosthesis, such as a stent-graft 111, is disposed on the device at a stent-graft retention region 105 and covered by retractable sheath 110. The delivery device further includes housing 112. Housing has a distal end 113, from which sheath 110 extends. Sheath 110 is fixed relative to housing 112 and is longitudinally movable with housing 112 over positioner 118. Housing 112 has a gripping portion 117 and a proximal portion 115. Housing 112 may include a hemostatic valve assembly (not shown) within housing 112. In a preferred example, the valve assembly is disposed in the proximal portion 115 of the housing 112 and be of the type set forth above. Housing 112 may have a port 144 and flushing tube 146 as described above with reference to FIG. 2. Deployment assist valve housing 116 with deployment assist valve sleeve 114 are slidably disposed relative to housing 112. As set forth above, deployment assist sleeve 114 is slidably disposed over positioner 118 and extends through an aperture in housing 112 at the proximal end 119 of housing 112 and reduces the frictional forces between the valve in the housing 112 and the positioner 118. As further shown in FIG. 4, handle assembly 101 includes a first handle 120 and a second handle 122 (shown with housing removed).

FIG. 5 is a partial exploded side view of the handle assembly 101 of delivery device 100 of FIG. 2. FIG. 5 shows the interior structure of the first 120 and second 122 handles. FIG. 6 is a partial view of the inner structure of first handle 120. FIG. 7 is a partial exploded view of the interior structure of first handle 120. As shown in FIG. 5, second handle 122 has been moved proximally to expose the interior structure of the second handle 122. Forward portion 120' of first handle 120 has been moved distally to expose the interior structure of the forward portion 120' of the first handle 120 and first handle housing 128 has been separated to show the internal structure of the first handle housing 128.

As shown in FIGS. 5, 6, and 7, the first handle housing 128 may comprise upper 128', 128" and lower parts that clam shell together. The parts lock together and are held together at the proximal end with ring 219 (best seen in FIG. 7). Forward portion 120' of first handle 120 may be made of a more flexible material, such as rubber, and includes grips 136.

Referring to FIGS. 6 and 12-15, inner cannula 148 extends through the delivery device 100 from the proximal end 102 to the nose cone dilator 108 (see FIG. 14). As shown in FIG. 14, disposed over inner cannula 148 is sealing rod 150 which may have an O-ring 152 at its proximal end. Sealing rod 150 has flared portion 154 at its distal end. Sealing rod 150 provides a conduit for trigger wires 151 as shown best in FIG. 14. Flared portion 154 is tapered and has a raised edge 160. Flared portion 154 may be made of a relatively hard plastic. The trigger wires 151 shown in FIGS. 14 and 15 extend from their respective trigger wire release mechanisms in the second handle 122, through the first handle 120 and into the sealing rod 150. Trigger wires 151 are held to cannula 148 by sealing ring 153 as shown in FIGS. 14 and 15. The sealing ring provides a very tight seal with the cannula 148. The sealing ring 153 also may have apertures in the sealing ring 153 through which the trigger wires 151 can pass as shown in FIG. 15. The sealing ring 153 preferably is a silicone disk. The sealing rod 150 and sealing ring 153 are disposed within first handle housing 128 (and hence within the slider rod 202) through aperture 205 (shown in FIG. 7). In this position, the O-ring 152 creates a seal between the sealing rod 150 and the slider rod 202. The proximal end 207 of the flared portion 154 of sealing rod 150 is disposed in the threaded portion 166 of the housing 128 as shown in FIG. 13. With the O-ring 152 and the sealing ring 153 in the lumen of the slider rod 202, the sealing ring 153 and the O-ring 152 cooperate to maintain hemostasis.

As shown in FIG. 6, disposed over the inner cannula 148 and at least partially within the lumen of sealing rod 150, and attached to sealing rod 150, is stiffener 156. Stiffener 156 may be attached to sealing rod 150 by being glued thereto. The stiffener 156 may be a stainless steel cannula which provides stiffening to the proximal end of the delivery device 100 for maneuverability and to prevent kinking in that region of the delivery device 100. Stiffener 156 extends beyond the distal end 157 of sealing rod 148 and into the lumen of positioner 118. Stiffener 156 may be between 20 cm and 40 cm long and preferably about 30 cm long. As such, the stiffener 156 extends from within the lumen of the sealing rod 150 and distally toward the distal end of the device 100 for about 30 cm.

As shown in FIG. 6, positioner 118 is disposed over stiffener 156 and extends through the delivery device to proximal the stent-graft retention region 105. As shown in FIGS. 23A and 23B, the distal end 121 of positioner 118 is tapered toward the outer diameter of the inner cannula 148. Inner cannula may have a polymer tubing over inner cannula 148. As shown in FIGS. 23A and 23B, positioner 118 may have an aperture 125 from which the distal trigger wire 252 or wires exits to engage the distal end of a prosthesis. A second aperture (not shown) may be provided for the wire to re-enter the positioner. At or about the point where the positioner 118 begins its taper, there is an area of increased diameter or a safety bump 123. After the implantation procedure has been completed, the physician may determine to leave the sheath in the body to use the lumen of the sheath as a conduit for other procedures. Hence, the physician may remove the delivery system sub-assembly including the handle assembly 101 and attached positioner 118 and nose cone dilator 108 by retracting them as a unit from within the sheath. The safety bump 123 at the end of the positioner 118, as it travels through the housing 112, engages the sleeve 114 and/or the deployment assist valve housing 116 of the deployment assist device 119 to ensure that the deployment assist device 119 is removed with the sub-assembly.

Positioner 118 has a flared proximal end 158 that sealingly engages with flared portion 154 of sealing rod 150. Flared proximal end 158 of positioner 118 is preferably of a softer material then flared portion 154. The relatively hard plastic of flared portion 154 compresses against the softer plastic of flared proximal end 158, indenting the plastic to seal the positioner to the first handle 120. This seal prevents the positioner 118 from moving relative to the handle 120 and creates a hemostatic seal. This is best shown in FIG. 13. As shown in FIG. 13, flared portion 154 of sealing rod 148 is sealing engaged within the first handle housing 128 at the threaded portion 166 of the first handle housing 128. When the threaded portion 166 is engaged with the inner threads of positioner cap 162, flared portion 154 of sealing rod 148 is sealingly engaged within the first handle housing 128.

As shown in FIGS. 6, 13 and 14, disposed over positioner 118 is positioner cap 162 having external threading or ridges 164 that engage with the interior (not shown) of the forward portion 120' of the first handle 120 to thereby hold the gripping portion 136 of the first handle 120 in place. Positioner cap 162 further may have internal threading 164 at its proximal end that engage with external threading 166 of first handle housing 128 to connect the positioner 118 to the first handle 120 by way of the threaded connection.

Second handle is discussed and described with reference at least to FIGS. 4, 9-10, 16-20 and 29-29. As shown, extending from the proximal end 102 of second handle 122 is a slider rod 202 that connects the first handle 120 to the second handle 122. The slider rod 202 is generally cylindrical in shape, but may include a flat surface 203 on one of its sides and has an inner lumen through which the inner cannula 148 extends. The slider rod 202 extends partially into the lumen of the first handle 120, to provide a small overlap within the first handle 120 and the second handle 122. The slider rod 202 is fixed relative to the first 120 and second handles 122. The slider rod 202 includes a trough 204 on its top surface 206 into which a safety lock rod 208 (shown in FIGS. 4, 16, and 17) is slidably disposed. As shown in FIGS. 16 and 17, which will be discussed in further detail below, safety lock rod assembly 207, includes safety lock rod 208 which has a key hole lock 210 configured to receive first safety pin 131 of first safety knob 130, and bevel 212. The key hole lock 210 is at the distal end of the safety lock rod 208 and the bevel 212 is at the proximal end of the safety lock rod 208. Key hole lock 210 has a straight portion 216 and a rounded portion 218.

As shown in FIG. 12, fixedly attached to slider rod 202 proximal of first handle 120 is a locking ring 220. Locking ring 220 is configured to receive safety pin 143 of second safety knob 142 in pin receiving aperture 222. When second safety pin 143 is disposed in receiving aperture 222, the second handle 120 is prevented from moving. Although the locking ring 220 is described and shown as a ring about the slider rod 202, other configurations are contemplated. Locking ring 202 also has upper and lower opposing channels into which protrusions 225 and 227 from rotation lock 224 extend to keep the locking ring from rotating.

As shown in FIG. 12, adjacent to locking ring 220 is rotation lock 224. Rotation lock prevents reverse rotation of second handle 122. Rotation lock 224 includes resilient fingers or flanges 226. The fingers 226 extend radially outwardly at a shallow angle in the same direction. Fingers 226 are shown fully in co-pending application Ser. No. 12/899,203 FIGS. 24 through 27, which figures and accompanying description is incorporated by reference herein. By providing corresponding abutments extending radially from the inner wall of the housing of the second handle 122, rotation of the housing of second handle 122 is allowed in one direction only while rotation in other direction is prevented. Rotation lock 224 does not itself rotate.

FIGS. 9, 10, and 11 show further features of the interior of second handle 122. Disposed about slider rod 202 and proximal to rotation lock 224 is a proximal wire(s) release mechanism 230. In the figures, the proximal wire(s) release mechanism 230 is shown as a threaded ring 230. As shown, threaded ring 230 has external threads 232 which engage corresponding threads (shown in FIGS. 26 and 27 as 237) on the interior of the housing of the second handle 122. Threaded ring 230 is longitudinally slidable over slider rod 202. Threaded ring 230 does not rotatably move on slider rod 202 due to an interior flat surface that corresponds to the flat surface 203 of slider rod 202. The conversion of the rotation force of the second handle 122 to the longitudinal motion of the threaded ring 230 results in a mechanical advantage for the user. Thereby this Archimedes screw principal is used to reduce the force exerted by the user on the system and in turn the force required to remove the trigger wires.

As best shown in FIGS. 10 and 11, threaded ring 230 has external threads 232 and a recess 235 which receives the proximal end or ends of one or more trigger wires 236 which extend from the threaded ring 230 through the delivery system to engage and retain the proximal end of a prosthesis retained on the delivery system. The end or ends of the trigger wires 236 may be held together by, for example, a clamp 234 as shown, which is disposed in recess 235 and which encapsulates the ends of the proximal trigger wire(s) 236. The operation of threaded ring trigger wire release mechanism 230 will be explained in further detail below in reference to FIGS. 28, 29 and 30.

As shown in FIGS. 10 and 11, next adjacent threaded ring 230 on slider rod 202 is safety rod ring 238 of the safety rod assembly 207 shown in FIGS. 16 and 17. The safety rod assembly is designed to prevent release of the stent-graft distal trigger wire(s) until the proximal trigger wire(s) have been released. Safety rod ring 238 is located at the proximal end 209 of safety lock rod 208. Key hole 210 is located at the distal end 211 of safety lock rod 208. As shown, safety lock road 208 is bent at an angle at its proximal end 209 to provide bevel 212. The bent portion 240 engages aperture 242 in safety rod ring 238 as shown in FIG. 16 at 239. The engagement is preferably a snap fit.

In a preferred arrangement, the safety lock rod 208 is stainless steel that has been heat-treated to a Rockwell hardness of between about 50 and 70 and preferably to a Rockwell hardness of between 58 and 60. The hardness adds to the strength of the metal but increases the brittleness allowing the rod 208 to break at the bevel 212 before it deforms in a circumstance where stress is applied to the rod. As the trough through which the rod slidably travels is preferably plastic, the ability for the rod to break prevents it from getting stuck if the handle is misused. The bevel 212 is a designed weak spot in the event the handle somehow misused. Hence, if the rod breaks at the bevel 212, releasing it from its attachment with the safety rod ring 238, the stent-graft can still be deployed Safety rod ring 238 is disposed about slider rod 202 with safety lock rod 208 disposed in trough 204 of slider rod 202. Key hole lock 210 has a straight portion 216 and a round portion 218 at the distal end of the straight portion 216. Key hole lock 210 is configured to receive first safety pin 131 of first safety knob 130 as shown in FIG. 17 at 241 as will be discussed in further detail with regard to FIGS. 18A-B to 20A-B below.

Referring again to FIGS. 10 and 11, adjacent the safety rod ring 238 on the slider rod 202 is the distal trigger wire(s) release mechanism 250. As shown in FIGS. 10 and 11, distal wire(s) release mechanism is a ring that is slidably disposed over slider rod 202. The proximal end(s) of one or more distal trigger wires 252 are held within a recess 254 in the distal trigger wire release mechanism 250. In one example, the end or ends of the one or more wires are clamped in the manner similar to the proximal trigger wire(s) as discussed above. The distal trigger wire(s) extend from the distal trigger wire release mechanism 250 to the distal end of the stent-graft. In one preferred example, as shown in FIGS. 10 and 11, the distal trigger wire or wires 252 pass through a trigger wire lumen 256 in the proximal trigger wire release mechanism 230, FIG. 18A is a side view of the first safety pin 131 of first safety knob 130. The pin 131 is threaded with at least two rotations of external threads 133. External threads 133 engage corresponding internal threads on the housing of the first handle 120. This threading arrangement allows for full engagement with the threads of the handle 120 and further allows for lock and unlock stops and makes removal of the knobs difficult. First safety pin 131 has a square or rectangular segment 135 at the key hole engaging end of the pin 131.

Figure 35:
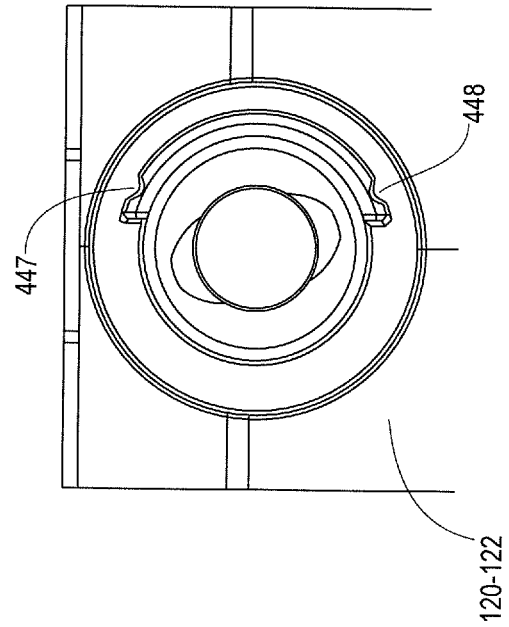
FIGS. 35 and 36 illustrate further details of the safety lock knob of at least FIGS. 18A-20B.
Figure 36:
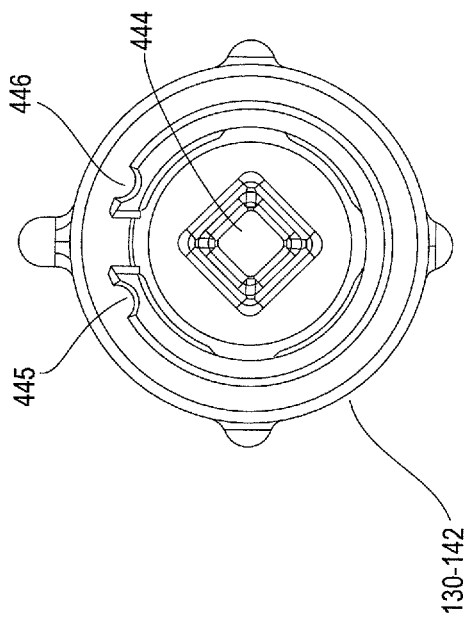

Prior to use of the delivery device 100 and after the stent-graft is loaded on the delivery device 100, first safety pin 131 is engaged with the straight portion 216 of the key hole lock 210. This locks the first safety knob 130 which prevents a physician from deploying the stent-graft distal end trigger wire(s) prior to releasing the stent graft proximal end trigger wire(s) 236. As shown in FIGS. 19B and 20B, the square or rectangular segment 135 of pin 131 is locked into place and prevented from turning in the straight portion 216. Straight section 216 has a small safety 243 protrusion. This safety 243, shown as a bump in the straight portion 216, also acts as a shipping safety and further guarantees that the safety lock rod is in the correct position. The position of the square or rectangular segment 135 of the pin 131 in the straight section prevents rotation of first safety knob, hence preventing premature deployment of the distal trigger wire(s). Furthermore, in one example and as shown in greater detail in FIGS. 35 and 36, the locking mechanism consists of the safety lock knob protruding detent 445/446 on safety lock knob 130/142 that mates with corresponding inset feature 447/448 on the handle 120/122. The pin (such as pin 131 shown in FIG. 26) is press fit circumferentially into the safety lock knob square 444 and therefore, forces are transferred from the pin 131 to the safety lock knob 130/142. The movement of the knob and subsequently the pin is therefore restrained to an 180 degree motion. Detent 446 begins in the inset 447, when the knob is rotated the knob and pin travel 180 degrees until detent 446 stops within inset 448.

Figure 26:
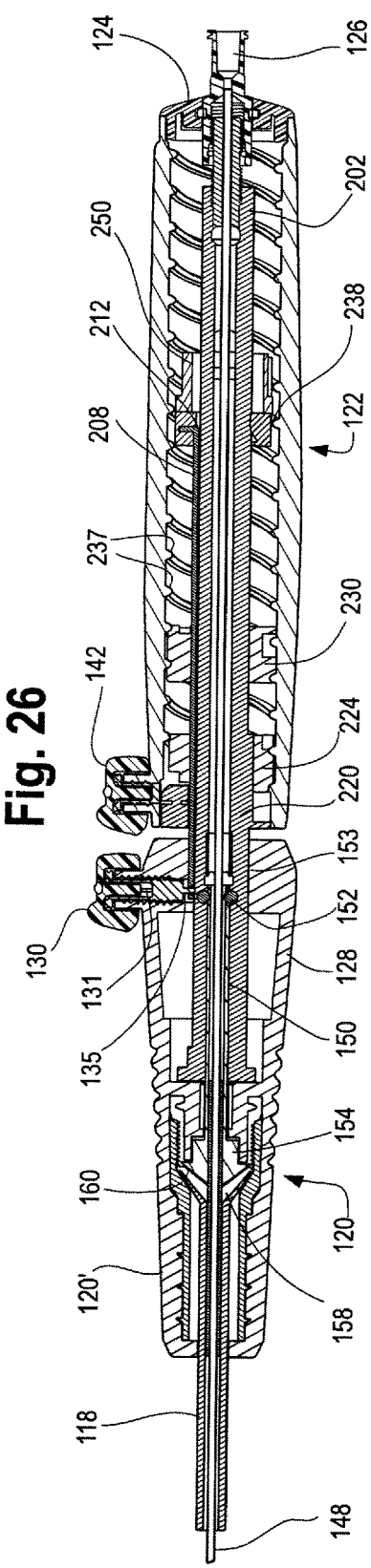
FIG. 26 is a schematic view of the interior structure of the handle assembly.
Figure 27:
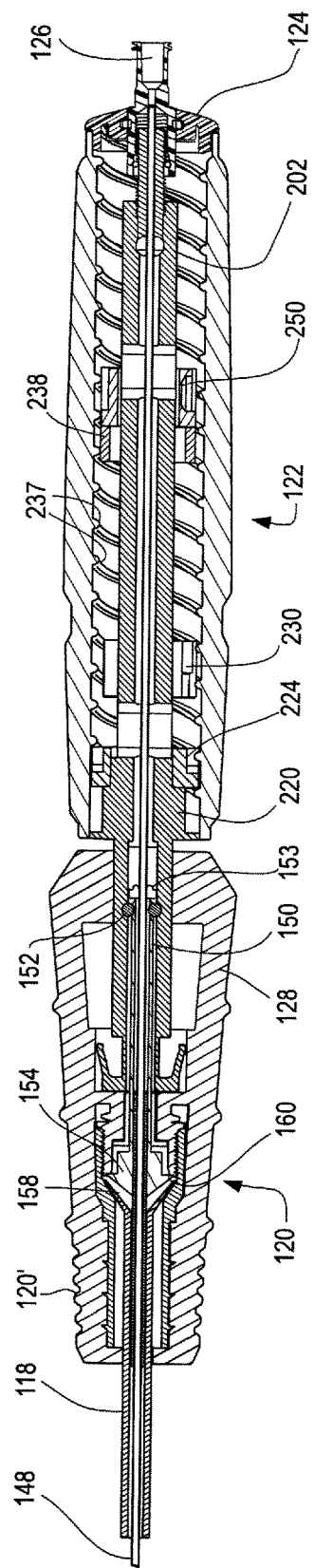
FIG. 27 is another schematic view of the interior structure of the handle assembly.

FIGS. 26 and 27 show schematic views of the handle assembly 101. From left to right, FIG. 26 shows inner cannula 148 which runs through the device to pin vice 127, 118 positioner, forward portion 120' of first handle 120, flared proximal end 158 of positioner 118, flared portion 154 with edge 160 of sealing rod 150, housing 128 of first handle 120, O-ring 152, sealing ring 153, first safety knob 130, first safety pin 131, square portion of safety pin 135, second handle 122, locking ring 220, rotation lock 224, proximal wire release mechanism (threaded ring) 230, inner threads 237, safety rod 208, bevel 212, safety rod ring 238, distal trigger wire release mechanism 250, slider rod 202, end cap 124 and pin vise 127. Similarly, from left to right, FIG. 27 shows, inner cannula 148 which runs through the device to pin vice 127, 118 positioner, gripping portion 120' of first handle 120, flared proximal end 158 of positioner 118, flared portion 154 with edge 160 of sealing rod 150, housing 128 of first handle 120, sealing rod 150, O-ring 152, sealing ring 153, second handle 122, locking ring 220, rotation lock 224, proximal wire release mechanism (threaded ring) 230, inner threads 237, safety rod ring 238, distal trigger wire release mechanism 250, slider rod 202, end cap 124 and pin vise 127.

Referring to FIGS. 18-20 and 28-32, the operation of the delivery device 100 in particular the handle assembly 101 of the delivery device will be described. In this example, use of the delivery device will be described in reference to the implantation of a stent-graft, such as the one showed in FIG. 1, in an aorta of a patient. After an incision is made in the femoral artery of the patient, the nose cone dilator is inserted into the incision and the device is advanced through the artery to the desired location, for example the abdominal aorta for placement of the stent-graft at the site of an aneurysm.

Figure 32:
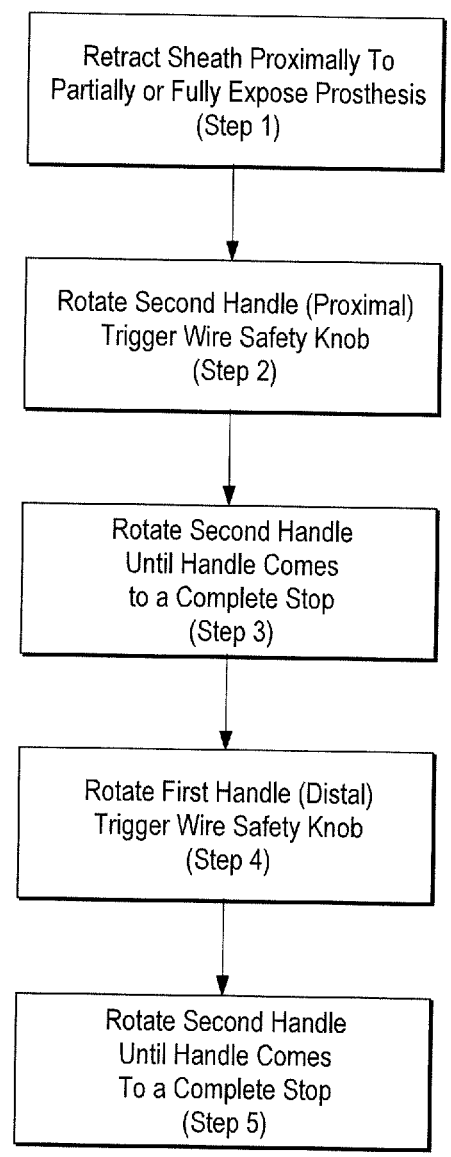
FIG. 32 is a flowchart of the steps for deployment.

FIG. 32 is a flow chart showing the basic steps of operation of the delivery device. In Step 1, the sheath is withdrawn proximally (toward the user) to partially or fully expose the prosthesis. In Step 2, the second handle (proximal) trigger wire safety knob is rotated approximately 180 degrees. In Step 3, the second handle is rotated until it comes to a complete stop. In Step 4, the first handle (distal) trigger wire safety knob 130 is rotated approximately 180 degrees. In Step 5, the second handle is rotated again until the handle comes to a complete stop.

Figure 33A:
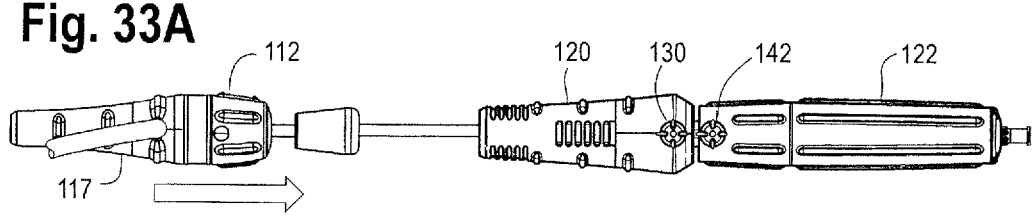
FIGS. 33A-F demonstrate the steps of FIG. 32.
Figure 33B:
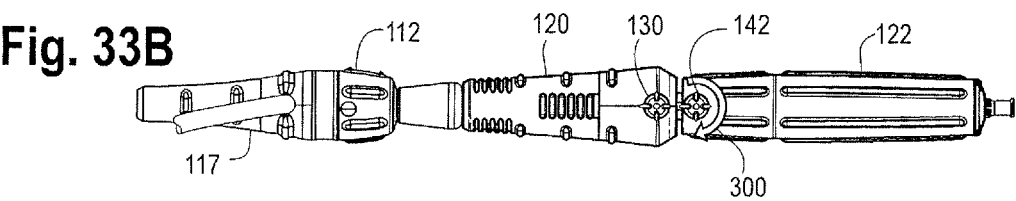

FIGS. 33A-F further demonstrates these steps. FIG. 33A shows the sheath withdrawal step. The user grasps the gripping portion 117 of housing 112 and pulls housing proximally (toward the user) in the direction of the arrow shown to partially or fully withdraw the sheath (not shown) from the prosthesis. Partial withdrawal may be desirable if re-positioning becomes necessary. FIG. 33B shows the housing in position once the sheath has been withdrawn.

Figure 33C:
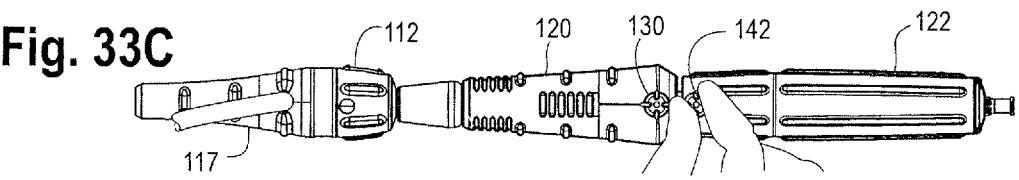

FIG. 33C (Step 2) shows the step of releasing the proximal trigger wire(s) from the proximal end of the prosthesis. In this step, the user rotates the second handle trigger wire safety knob 142, for example in the direction of the arrows 300, on the top of the knob 142. In this Figure, the arrows show a clockwise rotation. The rotation of knob 142 pulls the pin out of aperture 222 and releases the second handle 122 for rotation.

Figure 33D:
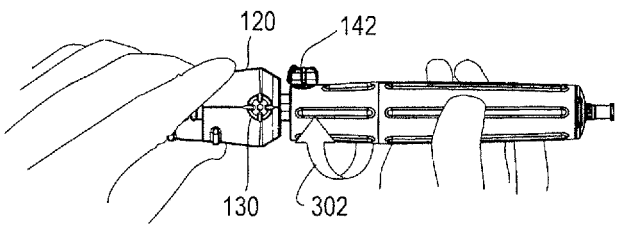
Figure 33E:
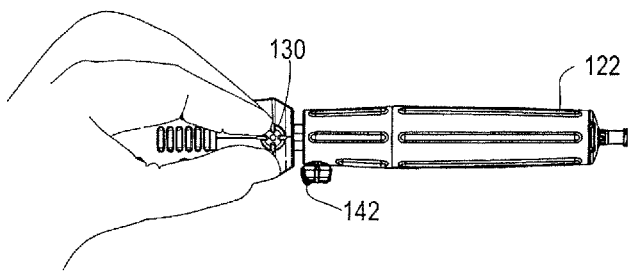

In FIG. 33D (Step 3), the second handle 122 is then rotated in the direction of the arrow 302 shown on the handle 142 (in this Figure, clockwise), though other constructions may use a counterclockwise rotation. By doing this, the inner threads 237 of the second handle 122 engage the outer threads 232 on the threaded ring 230 (the proximal trigger wire release mechanism) and the rotation of the handle causes the threaded ring to move proximally within the handle 122. Rotation continues until the handle 122 comes to a stop. At this point, the threaded ring has reached the safety rod ring 238.

In Step 4 (FIG. 33E), the user then rotates the first (distal) trigger wire safety knob 130 in the direction of the arrow 304 shown (in this Figure clockwise). This releases the pin 131 of knob 130 from the key hole lock 210 (as described in further detail below), permitting the safety rod to slide proximally in trough.

Figure 33F:
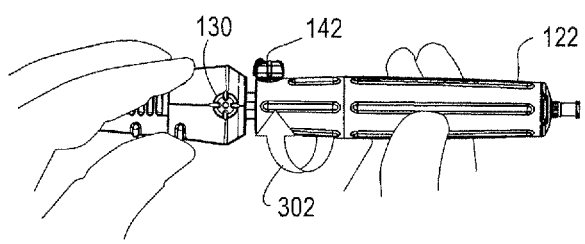

The user then moves on to Step 5 (FIG. 33F). In this step, the user then rotates the second handle 122 in the direction of the arrow 302 shown until the handle comes to a stop. By this action the distal trigger wire or wires are withdrawn from the distal end of the prosthesis.

In each rotation of the second handle 122, the respective trigger wires move only a few centimeters. For example, the first rotation of the handle that releases the proximal trigger wire or wires results in the threaded ring 230 traveling between 20-30 mm and a corresponding trigger wire travel. In one embodiment the threaded ring 230 travels is about 26 mm. The second rotation of the handle that results in the release of the distal trigger wire or wires the threaded ring travels another 20 to 30 mm for a total travel of about 50 mm to 70 mm. The distal wire or wires travel a corresponding distance to the second distance traveled by the threaded ring 230. In a delivery system, the shorter distance traveled by trigger wires, the less likely trigger wires are to become entangled on a device component. The wires are less likely to tangle during removal because they are not being withdrawn the full length of the system. Secondly, and importantly, rather than the proximal wires needing to be removed completely leaving behind distal wires, which greatly increases chances of the wires tangling, the proximal wires only travel a short length before both proximal and distal wires are withdrawn. In addition, the trigger wires remain in the delivery device and do not require complete withdrawal and removal from the system. Hence, much shorter trigger wires may be used.

The operation of the delivery device, and in particular the operation of the handle assembly, is described in further detail below with references to FIGS. 18-20 and 28-30. Upon determining by fluoroscopy, MRI, 3D or other imaging techniques that the delivery device is in the desired location, the user, with one hand on the grips 136 of the handle assembly and the other on the gripping portion 117 of housing 112, retracts the sheath 110 (proximally, i.e., toward the physician) until at least a proximal portion of the stent-graft is exposed. Alternatively, the physician may retract the sheath from the entire stent-graft.

FIGS. 24 and 25 show exemplary attachments for the trigger wires at the proximal and distal ends of the stent-graft of FIG. 1. As shown, distal trigger wire 400, which has exited a first aperture 402 in positioner 405, engages suture 404 which is attached to a limb 408 of the stent-graft. Distal trigger wire then re-enters positioner 405 through second aperture 406. FIG. 24 shows a similar attachment for the proximal end 410 of the stent-graft. As shown, trigger wires 412 exit from an aperture 414 in the delivery system, engage one or more apices 416 of the stent and re-enter a second aperture 418. The proximal end of the stent-graft may be held with multiple trigger wires. For example, each apex may be engaged by a trigger wire, or every other apex may be engaged by a trigger wire. A single trigger wire may engage two or more apices. Further, the trigger wires may exit and re-enter the delivery through the same aperture after engaging a portion of the stent graft. In another example, the trigger wires may engage sutures at the ends of the graft rather than apices.

At this point, the physician can release only the proximal end of the stent-graft. To release the proximal end of the stent-graft, the second safety knob 142 on the second handle is rotated in the direction of an arrow on the top of the knob (or set forth in the device's instructions for use) as discussed above and shown in FIG. 33. In one example, the safety knob 142 is rotated clockwise about 180 degrees. This removes the pin 143 of the safety knob 142 from engagement with aperture 222, hence releasing the second handle 122 for rotation. It should be noted that, at this point, because the square segment 135 of pin 131 is engaged in the straight section 216 of key hole lock 210, the first safety knob 130 of the first handle 120 cannot be rotated.

With second safety knob pin 143 rotated out of aperture 222 second handle 122 can rotate about the axis of the delivery device to retract and hence release the proximal trigger wires from the proximal end of the stent-graft. Rotation of the second handle 122, for example in a clockwise direction, engages the inner threads of the second handle 122 with the external threads of the threaded ring 230 (proximal wire release mechanism) causing the threaded ring 230 to move in the proximal direction in the second handle 122 as indicated by the arrow in FIG. 29 (i.e., toward the physician). The handle 122 is rotated until it comes to a stop when it engages the safety rod ring 238 as shown in FIG. 29. The proximal movement of the threaded ring 230 pulls the proximal trigger wires 236 proximally thereby releasing them from the proximal end of the stent graft, which in turn releases the proximal end of the stent graft. This step must be performed before the physician can release the distal trigger wire(s).

At this point, the square portion of pin 131 of first trigger wire safety knob is disposed in the straight portion 216 of key hole lock 210. As shown in FIG. 19B, because of the safety 243 in the straight portion 216, a slight further rotation may be required to pull the safety rod back (in the direction of the arrow shown in FIG. 20B) to move the safety 243 past the square portion of pin 131 such that the square portion of the pin is in the round portion 218 of key lock 210. As the threaded ring 230 engages the safety rod ring 238, Only at this point can the first trigger wire safety knob 130 be rotated. However, because the pin 131 is still engaged in the key hole lock 210 the threaded ring 230 cannot move further until the physician rotates the first trigger wire safety knob pin 131 out of the round portion 218 of the key hole lock 210. Upon rotation of the first trigger wire safety knob 130, for example clockwise about 180 degrees, the pin 131 is removed from engagement with the key hole lock 210.

Once the first safety knob pin 131 is removed from engagement with the key hole lock 210, the threaded ring 230 may one more move proximally upon rotation of the second handle 122. As the threaded ring 230 moves proximally, it in turn moves both the safety rod ring and the distal trigger wire release mechanism proximally, in the direction of the arrow shown in FIG. 30, until a stop is reached at the back of the device. The stop may be a separate component or may merely be the back of end cap 124. This movement of the distal trigger wire release mechanism pulls the distal trigger wire or wires proximally, thereby disengaging the wire or wires from the distal end of the stent-graft.

Turning now to FIGS. 34A-34F, the steps of an emergency "bailout" procedure are described. As set forth above, second handle 122 can rotate about the axis of the delivery device to retract and release the trigger wires from the respective proximal and distal ends of the stent graft during deployment. However, in the event that any portion of the delivery device fails or the system otherwise malfunctions such that the stent graft cannot completely released, the bailout procedure provides the user the ability to manually deploy the stent graft, and more specifically, to manually withdraw the proximal and/or distal trigger wires.

Figure 34A:
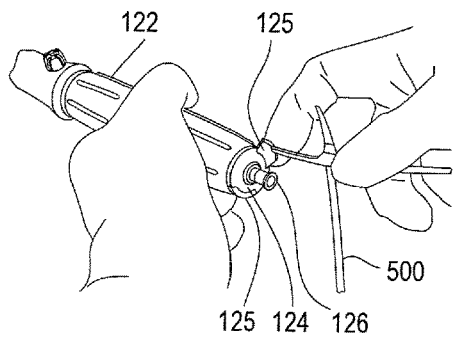
FIGS. 34A-F demonstrate the steps of an emergency "bailout" procedure.
Figure 34B:
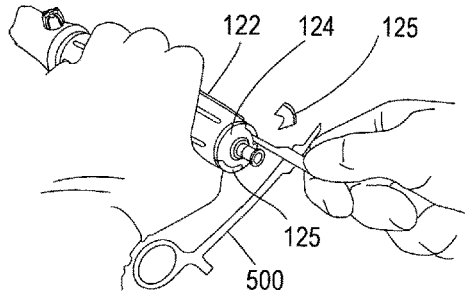

In the first steps as shown in FIGS. 34A and 34B, the user can firmly grip handle 122 with one hand, and using a tool such as surgical forceps 500 or the like, can snap out or otherwise remove indentations 125 from the back end cap 124. In the illustrated Figures, there are two indentations that may be removed from end cap 124.

Figure 34C:
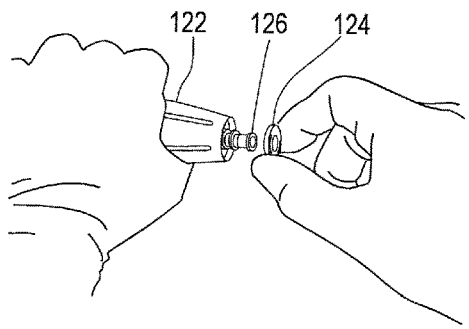

Next, as shown in FIG. 34C, removal of one or more of indentations 125 allows the end cap 124 to become loosened such that it can be manually removed and separated from the proximal end 140 of handle 122.

Figure 34D:
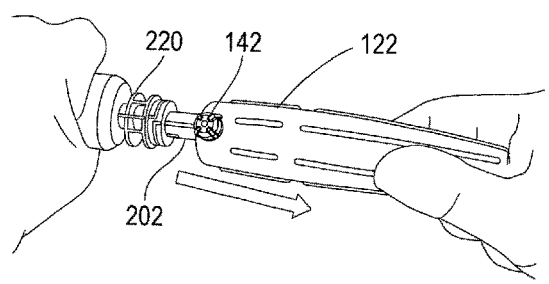
Figure 34E:
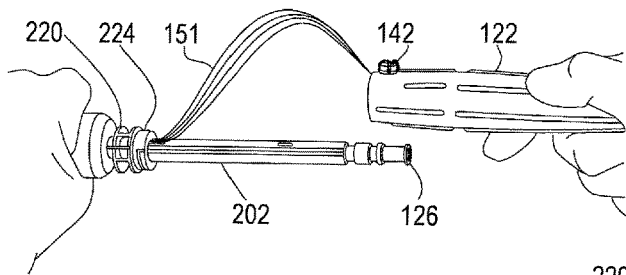

At this time, as shown in FIG. 34D, handle 122 can be slid proximally towards the user and removed so that the inner components of the handle are exposed. As shown in FIG. 34D, the sliding rod 202 is now visible with one or more proximal and/or distal trigger wires extending proximally (towards the user) from the device from a location proximal to locking ring 220 and rotation lock 224. The trigger wires will pull out with the removal of handle 122.

Figure 34F:
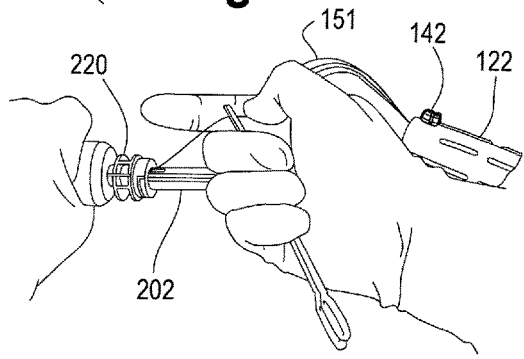

If it becomes necessary in order to properly deploy the proximal and/or distal end of the stent graft, one or more of the proximal and/or distal trigger wires 151 may be removed individually by hand or with tool 500 as shown in FIG. 34F.

The invention claimed is:

1. A handle assembly for a prosthesis delivery device, the handle assembly comprising:
   an axially slidable handle comprising a housing and a slidable and retractable sheath attached to and extending from a distal end of the housing;
   a fixed handle proximal of the axially slidable handle that is fixed relative to the delivery system and comprising a housing having a distal end and a proximal end, and a fixed handle locking mechanism;
a rotatable handle proximal of the fixed handle that is rotatable relative to the delivery system and comprising:
a housing having a distal end and a proximal end;
a rotatable handle locking mechanism preventing rotation of the rotatable handle;
a prosthesis proximal end release mechanism disposed in the housing of the rotatable handle and releasably and operatively connected to a proximal end of a prosthesis;
a prosthesis distal end release mechanism disposed in the housing of the rotatable handle and releasably and operatively connected to a distal end of a prosthesis;
wherein the slidable handle is slidable in a proximal direction to proximally retract the sheath from over the prosthesis;
wherein unlocking of the rotatable handle locking mechanism permits a first rotation of the rotatable handle to release the proximal end of the prosthesis from the delivery system;
wherein a subsequent unlocking of the fixed handle locking mechanism permits a second rotation of the rotatable handle to release the distal end of the prosthesis from the delivery system;
wherein the distal end of the prosthesis cannot be released from the delivery system until the proximal end of the prosthesis is released from the delivery system; and
wherein the fixed handle locking mechanism cannot be unlocked until the rotatable handle locking mechanism is unlocked.

2. The handle assembly of claim 1, wherein the fixed handle is directly distally adjacent to the rotatable handle.

3. The handle assembly of claim 1, wherein the fixed handle is fixed relative to the prosthesis delivery device, and the rotatable handle is rotatable relative to the fixed handle and the slidable handle.

4. The handle assembly of claim 1, including a slider rod extending longitudinally at least partially through the fixed handle and the rotatable handle.

5. The handle assembly of claim 4, wherein the slider rod comprises a safety lock assembly.

6. The handle assembly of claim 5, wherein the fixed handle locking mechanism comprises a first safety knob disposed exterior to the fixed handle housing and a first safety pin attached to the first safety knob and extending from the first safety knob and through the fixed handle housing to engage the safety lock assembly.

7. The handle assembly of claim 6, wherein the fixed handle safety knob is prevented from turning until after the first rotation of the rotatable handle is complete.

8. The handle assembly of claim 1, wherein the prosthesis proximal end release mechanism comprises a threaded ring.

9. The handle assembly of claim 1, wherein the prosthesis proximal end release mechanism is operatively engaged with the rotatable handle and the proximal end of the prosthesis such that upon the first rotation of the rotatable handle, the prosthesis proximal end release mechanism moves axially within the rotatable handle to release the proximal end of the prosthesis.

10. A handle assembly for a prosthesis delivery device comprising a distal end and a proximal end:
a substantially immoveable first handle comprising a housing and a first handle locking assembly;
a rotatable handle comprising:
a housing having an interior surface;
a rotatable handle locking assembly extending from external of the housing to an interior of the housing to prevent rotation of the rotatable handle;
a first axially moveable element disposed within the housing and engaging the interior surface of the housing, the first axially moveable element further having at least one first trigger wire extending distally from the first axially moveable element to a proximal end of a prosthesis to releaseably engage the proximal end of the prosthesis;
a second axially moveable element disposed proximal of the first axially moveable element and having at least one second trigger wire extending distally from the second axially moveable element to a distal end of the prosthesis to releaseably engage the distal end of the prosthesis;
wherein the first handle locking assembly is prevented from unlocking until after a first rotation of the rotatable handle advances the first axially moveable element to release the at least one first trigger wire from the proximal end of the prosthesis.

11. The handle assembly of claim 10, wherein the first handle locking assembly comprises a knob, a knob pin extending from the knob, a safety lock rod and a slider rod at least partially longitudinally disposed through the housing of the first handle, wherein the slider rod comprises a longitudinal trough formed in a surface of the slider rod, and the safety lock rod is disposed in the trough of the slider rod, wherein the knob pin extends through the housing of the first handle and releasably engages the safety lock rod.

12. The handle assembly of claim 10, wherein the at least one second trigger wire cannot be released from the prosthesis until after the at least one first trigger wire is released from the prosthesis.

13. The handle assembly of claim 10, wherein the first handle locking assembly cannot be unlocked until after the rotatable handle locking assembly is unlocked.

14. The handle assembly of claim 10, wherein the first axially moveable element and the second axially moveable element are not rotatable.

15. A delivery system for delivering a prosthesis comprising:
a proximal end;
a distal end;
a prosthesis retention region;
a prosthesis having a proximal end and a distal end disposed at the prosthesis retention region; and
a handle assembly comprising:
a first handle comprising a housing having a distal end and a proximal end, and a first handle locking mechanism;
a rotatable handle comprising:
a housing having a distal end and a proximal end;
a rotatable handle locking mechanism preventing movement of the rotatable handle;
a prosthesis proximal end release mechanism disposed in the housing of the rotatable handle and operatively connected to the proximal end of the prosthesis;
a prosthesis distal end release mechanism disposed in the housing of the rotatable handle and operatively connected to the distal end of the prosthesis;
wherein unlocking of the rotatable handle locking mechanism permits a first rotation of the rotatable handle to release the proximal end of the prosthesis from the delivery system;

wherein unlocking of the first handle locking mechanism permits a second rotation of the rotatable handle to release the distal end of the prosthesis from the delivery system; and wherein the first handle locking mechanism cannot be unlocked until the rotatable handle locking mechanism is unlocked.

16. The delivery system of claim 15, wherein the distal end of the prosthesis cannot be released from the delivery system until after the proximal end of the prosthesis is released.

* * * * *